(12) United States Patent
Evers et al.

(10) Patent No.: US 9,772,272 B2
(45) Date of Patent: Sep. 26, 2017

(54) SUBSTANCE DETERMINING APPARATUS

(75) Inventors: Toon Hendrik Evers, Eindhoven (NL); Johannes Joseph Hubertina Barbara Schleipen, Eindhoven (NL); Joannes Baptist Adrianus Dionisius Van Zon, Eindhoven (NL); Derk Jan Wilfred Klunder, Eindhoven (NL); Josephus Arnoldus Hendricus Maria Kahlman, Eindhoven (NL); Ron Martinus Laurentius Van Lieshout, Eindhoven (NL); Mikhail Mikhaylovich Ovsyanko, Eindhoven (NL); Kim Van Ommering, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 490 days.

(21) Appl. No.: 13/498,615

(22) PCT Filed: Sep. 24, 2010

(86) PCT No.: PCT/IB2010/054304
§ 371 (c)(1),
(2), (4) Date: Mar. 28, 2012

(87) PCT Pub. No.: WO2011/036638
PCT Pub. Date: Mar. 31, 2011

(65) Prior Publication Data
US 2012/0202194 A1    Aug. 9, 2012

(30) Foreign Application Priority Data

Sep. 28, 2009 (EP) .................................. 09171484

(51) Int. Cl.
| | | |
|---|---|---|
| *G01N 15/06* | (2006.01) | |
| *G01N 15/14* | (2006.01) | |
| *G01N 21/47* | (2006.01) | |
| *G01N 21/552* | (2014.01) | |
| *G01N 21/64* | (2006.01) | |
| *G01N 27/74* | (2006.01) | |
| *G01N 33/543* | (2006.01) | |
| *G01N 15/02* | (2006.01) | |
| *G01N 35/00* | (2006.01) | |

(52) U.S. Cl.
CPC ..... *G01N 15/0612* (2013.01); *G01N 15/1434* (2013.01); *G01N 21/47* (2013.01); *G01N 21/552* (2013.01); *G01N 21/648* (2013.01); *G01N 27/745* (2013.01); *G01N 33/54333* (2013.01); *G01N 35/0098* (2013.01); *G01N 2015/025* (2013.01); *G01N 2201/0627* (2013.01)

(58) Field of Classification Search
CPC ........... G01N 15/0612; G01N 15/1434; G01N 21/47; G01N 21/552; G01N 21/648; G01N 27/745; G01N 33/54333; G01N 35/0098; G01N 2015/025; G01N 2201/0627
See application file for complete search history.

(56) References Cited

U.S. PATENT DOCUMENTS

| | | |
|---|---|---|
| 4,081,244 A | 3/1978 | Polito |
| 5,719,063 A | 2/1998 | Block |
| 6,592,822 B1 * | 7/2003 | Chandler .................. 422/82.05 |
| 2003/0007896 A1 | 1/2003 | Tiefenthaler |
| 2003/0232388 A1 | 12/2003 | Kreimer |
| 2005/0087000 A1 | 4/2005 | Coehoorn |
| 2005/0227231 A1 | 10/2005 | Tcherkassov |
| 2007/0172890 A1 | 7/2007 | Prins |
| 2008/0206104 A1 | 8/2008 | Prins |
| 2008/0213910 A1 | 9/2008 | Jogikalmath |

FOREIGN PATENT DOCUMENTS

| | | |
|---|---|---|
| JP | 2009025193 A | 2/2009 |
| WO | 0120330 A1 | 3/2001 |
| WO | 2008010110 A1 | 1/2008 |
| WO | 2008107847 A1 | 9/2008 |
| WO | 2009006409 A2 | 1/2009 |
| WO | 2009037636 A1 | 3/2009 |
| WO | 2009081136 A2 | 7/2009 |
| WO | 2009083814 A2 | 7/2009 |
| WO | 2009098623 A1 | 8/2009 |
| WO | 2010026551 A1 | 3/2010 |

OTHER PUBLICATIONS

Pamme, Magnetism and Microfluidics, Lab on a Chip, 6:24-28, 2006.*
PerkinElmer, An Introduction to Fluorescence Spectroscopy, p. 1-36, 2000.*
Hegner, Martin "DNA Handles for Single Molecule Experiments" Single Molecules, vol. 1, No. 2, 2000, pp. 139-144.

* cited by examiner

Primary Examiner — Andrea S Grossman

(57) ABSTRACT

A substance determining apparatus determines a substance within a fluid where particles, which have attached the substance, are bound to a binding surface. A sensing unit is configured to generate a sensing signal being indicative of at least one of i) a distance between the particles bound on the binding surface and the binding surface, and ii) an in-plane position of the particles bound on the binding surface. A binding discrimination unit is configured to discriminate between different kinds of binding of the particles bound on the binding surface depending on the generated sensing signal. The binding discrimination unit may be a unit for determining the part of the sensing signal being caused by specifically bound particles and for determining the substance based on this determined part of the sensing signal.

8 Claims, 9 Drawing Sheets

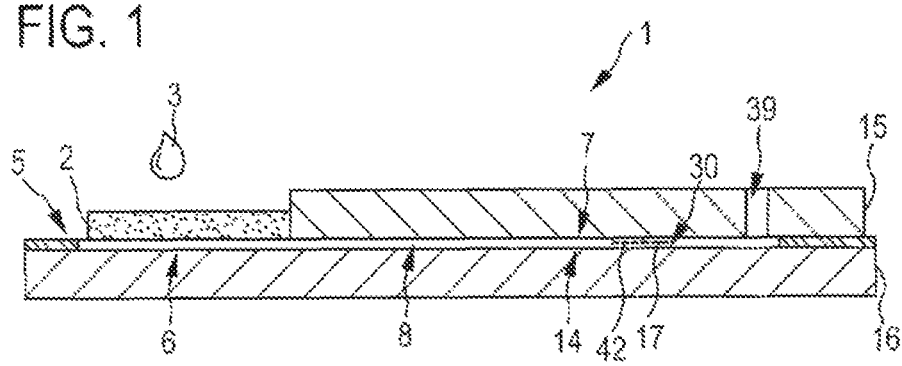
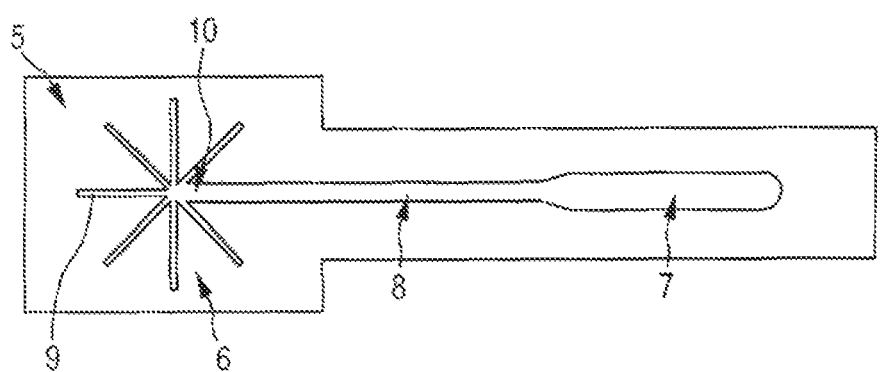
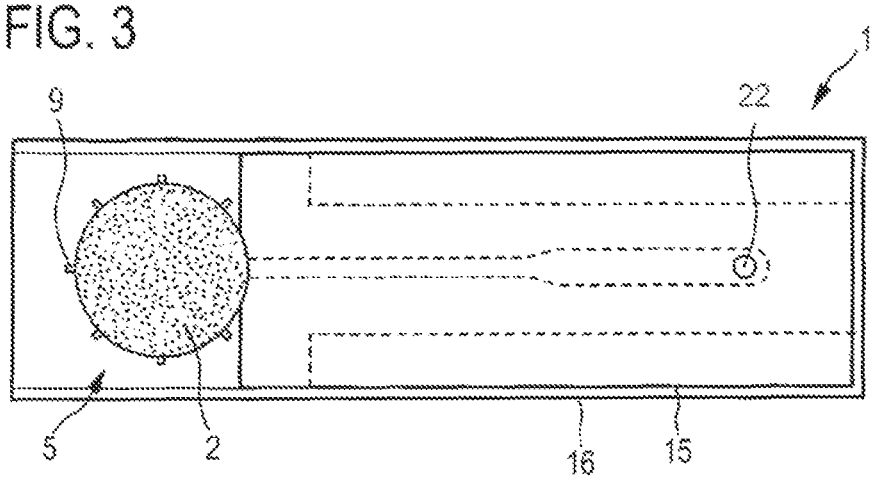

SUBSTANCE DETERMINING APPARATUS

FIELD OF THE INVENTION

The invention relates to a substance determining apparatus and substance determining method for determining a substance within a fluid. The invention relates further to a binding device and an analyzing device for cooperating with each other for determining a substance in a fluid, to a binding method and an analyzing method for cooperating with each other for determining a substance in a fluid, and an analyzing computer program for determining a substance within a fluid.

BACKGROUND OF THE INVENTION

WO 2009/098623 A1 discloses a magnetic biosensor based on magnetic beads that can be actuated with electromagnetic fields. The magnetic beads are functionalized with antibodies that can bind a specific analyte molecule in a sample. The beads are attracted to the sensor surface, where the number of bound beads is directly or inversely related to the amount of analyte molecules present in the sample. The beads are then detected by a technique which is based on frustrated total internal reflection (FTIR).

SUMMARY OF THE INVENTION

When measuring low analyte concentrations, the sensitivity is generally determined by the signal that is obtained for a low concentration and the signal that is obtained for a blank measurement, containing no analyte. It is observed that the signal for the blank measurement is not only determined by instrument noise, but that an additional signal is generated by beads binding to the surface, independent of the presence of an analyte, i.e. that an additional signal is generated by non-specific binding. Since this non-specific binding occurs, increasing the instrumental signal per bead does not increase the overall sensitivity, as the signal for the non-specific binding is also increased.

It is an object of the present invention to provide a substance determining apparatus and substance determining method for determining a substance within a fluid, which allows increasing the sensitivity of determining the substance. It is a further object of the present invention to provide a corresponding binding device and analyzing device for cooperating with each other for determining a substance in a fluid, a binding method and an analyzing method for cooperating with each other for determining a substance in a fluid, and an analyzing computer program for determining a substance within a fluid.

In a first aspect of the present invention a substance determining apparatus for determining a substance within a fluid is presented, wherein the substance determining apparatus comprises:
  particles for being attached to the substance within the fluid
  a binding surface for binding the particles, if the particles have been attached to the substance,
  a sensing unit for sensing the particles on the binding surface, wherein the sensing unit is adapted to generate a sensing signal being indicative of at least one of i) a distance between the particles bound on the binding surface and the binding surface and ii) an in-plane position of the particles bound on the binding surface,
  a binding discrimination unit for discriminating between different kinds of binding of the particles bound on the binding surface depending on the generated sensing signal.

Since the kind of binding generally differs in at least one of i) the distance to the binding surface and ii) the in-plane position on the binding surface, by generating a sensing signal being indicative of at least i) the distance to the binding surface and ii) the in-plane position on the binding surface, a signal is determined being indicative of the kind of binding, i.e., in particular, being indicative of non-specific and specific binding. This signal can therefore be used to discriminate between different kinds of binding of the particles bound on the binding surface, for example, to determine the amount or concentration of particles bound by a first kind of binding and the amount or concentration of particles bound on the binding surface by a second kind of binding. The substance determining apparatus allows therefore determining particles which are bound to the binding surface by a certain kind of binding. This allows therefore improving the sensitivity of the substance determining apparatus for particles bound to the binding surface by a certain kind of binding.

In particular, since non-specific binding and specific binding generally differs in distance to the binding surface and/or the in-plane position, by generating a sensing signal being indicative of a distance to the binding surface and/or the in-plane position, a signal can be determined being indicative of non-specific and specific binding. This signal can therefore be used to distinguish between non-specific and specific binding and to determine the particles on the binding surface, which are specifically bound, i.e. which have been attached to the substance, for example, to determine the amount or concentration of these particles and, thus, of the substance. Since this determined amount or concentration is not affected by non-specific binding, the sensitivity of determining the substance can be increased.

The in-plane position of a particle bound on the binding surface is preferentially the position of the particles within a plane defined by the binding surface, in particular, being parallel to the binding surface.

The binding discrimination unit is preferentially a unit for determining the part of the sensing signal being caused by a certain kind of binding, in particular, for determining the part of the sensing signal being caused by specifically bound particles, depending on the generated sensing signal. The binding discrimination unit is preferentially further adapted to determine the concentration and/or amount of the substance within the fluid depending on the determined part of the sensing signal being caused by a certain kind of binding, in particular, on the determined part of the sensing signal being caused by specifically bound particles.

The substance determining apparatus is preferentially a magnetic biosensor, wherein the particles are magnetic beads, i.e. nanoparticles, which label the substance. The magnetic beads are preferentially functionalized with an attaching element that can be attached to the substance being, for example, a specific analyte molecule. The attaching element is, for example, an antibody, a protein, DNA, an aptamer et cetera.

The substance determining apparatus preferentially comprises a magnetic unit for attracting the magnetic beads to the binding surface and/or for pulling the magnetic beads away from the binding surface.

The sensing unit can be any unit which uses a technique that allows generating a sensing signal being dependent on the distance of the particles from the binding surface.

The binding discrimination unit is preferentially a specific binding determination unit for determining a substance within a fluid, wherein the specific binding determination unit is adapted for determining specifically bound particles being particles bound to the binding surface, which have been attached to the substance, depending on the generated sensing signal.

A specific binding is preferentially a binding that depends on the presence of the substance, i.e. it preferentially describes a binding, wherein a particle has been attached to the substance and is bound to the binding surface, whereas non-specific binding is preferentially a binding that is not dependent on the presence of the substance, i.e. it preferentially describes a presence of particles on the binding surface, wherein the particles have not been attached to the substance.

The substance determination apparatus is preferentially a biosensor, in particular, a biosensor being adapted to perform a sandwich immunoassay.

The specific binding determination unit is preferentially adapted to determine the amount of specifically bound particles on the binding surface.

It is preferred that the sensing unit comprises a light source for generating radiation for being directed to the binding surface for generating an evanescent field and a light detector for detecting light from the binding surface and being indicative of an influence of the particles on the evanescent field, wherein the sensing unit is adapted to generate the sensing signal based on the detected light.

The evanescent field on the binding surface decays with increasing distance to the binding surface and can therefore be used to generate a sensing signal being dependent on the distance of the particles from the binding surface, wherein the sensing signal is sensitive for small variations of distances between the particles and the binding surface. In particular, the sensing signal is sensitive for a variation of the distance of 100 nm or smaller, further preferred of 50 nm or smaller, and even further preferred of 1 nm.

It is also possible to use another sensing unit which is based on another technique being sensitive to the distance of the particles to the binding surface. For example, a giant magneto resistance (GMR) technique or a fluorescence resonance energy transfer (FRET) technique can be used by the sensing unit.

It is further preferred that the sensing unit is adapted to modify at least one of i) the distance between the particles bound to the binding surface and the binding surface, ii) the in-plane position of the particles bound on the binding surface and iii) a distance sensitivity of the sensing unit, wherein the distance sensitivity is indicative of the dependence of the sensing signal on the distance between the particles bound to the binding surface and the binding surface, and to generate a first sensing signal depending on at least one of i) a first distance between the particles bound to the binding surface and the binding surface, ii) a first in-plane position of the particles bound on the binding surface and iii) a first distance sensitivity, and to generate a second sensing signal depending on at least one of i) a second distance between the particles bound to the binding surface and the binding surface, ii) a second in-plane position of the particles bound to the binding surface and iii) a second distance sensitivity, wherein the binding discrimination unit is adapted to discriminate between different kinds of binding depending on the first sensing signal and the second sensing signal.

Preferentially, the binding discrimination unit is a specific binding determination unit that is adapted to determine the specifically bound particles depending on the first sensing signal and the second sensing signal.

In particular, the sensing unit comprises a light source for generating radiation for being directed to the binding surface for generating an evanescent field and a light detector for detecting light from the binding surface and being indicative of an influence of the particles on the evanescent field, wherein the sensing unit is adapted to generate the sensing signal based on the detected light, wherein the sensing unit is adapted to modify the spatial relationship between the evanescent field and the particles bound to the binding surface by modifying at least one of i) the distance between the particles bound to the binding surface and the binding surface, ii) the in-plane position of the particles bound on the binding surface, and iii) the distance sensitivity, to generate the first sensing signal depending on a first spatial relationship between the evanescent field and the particles bound to the binding surface, and to generate the second sensing signal depending on a second spatial relationship between the evanescent field and the particles bound to the binding surface.

The distance sensitivity defines preferentially the intensity of a sensing signal, if the respective particle is present at a certain distance to the binding surface. Thus, if a first measurement is performed with a first distance sensitivity and a second measurement is performed with a second distance sensitivity being different to the first distance sensitivity, a first sensing signal being the result of the first measurement and a second sensing signal being the result of the second measurement are different, if the respective particles bound to the binding surface have the same distance to the binding surface. The distance sensitivity can, for example, be modified by modifying the evanescent field, in particular, by modifying the height of the evanescent field.

The spatial relationship between the evanescent field and the particles bound to the binding surface is preferentially the spatial relationship in a direction orthogonal to the binding surface. Thus, the spatial relationship is preferentially the relationship between the height of the evanescent field and the distance of the particles to the binding surface. The intensity I(z) of the evanescent field at a distance z from the surface can be written as: $I(z) \sim \exp(-z/\zeta)$ where the evanescent field decay length $\zeta$ is given by $$\zeta = \frac{\lambda}{4\pi\sqrt{n_1^2 \sin^2\theta - n_2^2}}$$

with $\lambda$ being the wavelength of the light, $n_1$ and $n_2$ being the refractive indices of the substrate and the sample liquid respectively, and $\theta$ being the entrance angle with respect to the cartridge surface normal of the light beam used for generating the evanescent field. The intensity of the light being scattered and/or absorbed by a particle bound to the surface at a distance z is then given by $I^{part.}_{scat/abs}(z) \sim \sigma_{part.}(d,\lambda) \cdot \exp(-z/\zeta(\lambda))$ where $\sigma_{part}(d,\lambda)$ is the scattering and/or absorption cross section of the particle with diameter d at wavelength $\lambda$. The evanescent field decay length $\zeta$ can be regarded as the height of the evanescent field. However, it should be noted that the evanescent field decays exponentially with increasing distance to the binding surface, i.e. mathematically at each distance to the binding surface an evanescent field can still be present.

The sensing unit can be adapted to generate more than two sensing signals depending on more than two different spatial relationships between the evanescent field and the particles bound to the binding surface, wherein the specific binding determination unit can be adapted to determine the specifically bound particles depending on the generated different sensing signals being more than two signals only.

The sensing unit can also be adapted to generate more than two evanescent fields, in order to generate more than two sensing signals.

It is further preferred that the sensing unit is adapted to modify the relationship between the evanescent field and the particles bound to the binding surface by modifying the wavelength of the radiation being directed to the binding surface.

In an embodiment, the light source is adapted to generate first radiation having a first wavelength for being directed to the binding surface and for generating a first evanescent field and second radiation having a second wavelength for being directed to the binding surface and for generating a second evanescent field, wherein the light detector is adapted to detect the first radiation and the second radiation after having been reflected or scattered from the binding surface, wherein the light detector is adapted to generate the first sensing signal depending on the detected first radiation and to generate the second sensing signal depending on the detected second radiation.

This allows generating a first evanescent field and a second evanescent field by simply using two different wavelengths. Furthermore, since different wavelengths are used, the first sensing signal and the second sensing signal can easily be generated by measuring the first radiation having the first wavelength and the second radiation having the second wavelength by the light detector from the binding surface. The light detector is preferentially adapted to distinguish the first wavelength and the second wavelength. Alternatively or in addition, the sensing unit can be adapted to illuminate the binding surface first with a first radiation and then with a second radiation or vice versa. In this case, the light detector does not need to distinguish between the first wavelength and the second wavelength.

Since the two evanescent fields have different dependencies on the distance from the binding surface, influences of the different evanescent fields by the particles on the binding surface are indicative of particles located at different distances to the binding surface. Since different bindings, in particular, specific and non-specific binding, are different with respect to the distance to the binding surface, the first sensing signal and the second sensing signal can be used for discriminating between different kinds of binding, in particular, for determining specifically bound particles.

The light source comprises preferably two light emitting diodes (LEDs) for generating the different wavelengths. In particular, the light source preferentially comprises a red LED and a blue LED. However, the light source can also comprise a red laser and a blue laser for exciting an evanescent filed.

It is further preferred that the sensing unit is adapted to modify the relationship between the evanescent field and the particles bound to the binding surface by modifying the angle under which the radiation meets the binding surface.

In an embodiment, the light source is adapted to generate first radiation being directed to the binding surface under a first angle for generating the first evanescent field and second radiation being directed to the binding surface under a second angle for generating the second evanescent field, wherein the light detector is adapted to detect the first radiation and the second radiation after having been reflected or scattered at the binding surface, wherein the sensing unit is adapted to generate the first sensing signal depending on the detected first radiation and to generate the second sensing signal depending on the detected second radiation. The first and second radiation can have the same wavelength.

This allows simply generating two evanescent fields by using two different angles under which the first radiation and the second radiation, respectively, meet the binding surface. Furthermore, since the reflected first radiation and the reflected second radiation point into different directions, in the case of using a FTIR technique the reflected first radiation and the reflected second radiation can easily be separated from each other by detecting these radiations at different spatial positions.

Also more than two wavelengths and/or more than two angles, under which the radiation is directed to the binding surface, can be used. Furthermore, radiation having different wavelengths and being directed to the binding surface under different angles can be used.

The sensing unit can also be adapted to change the refractive index of the fluid, for example, by exchanging the fluid by another fluid, thereby modifying the evanescent field, in particular, the height and distance sensitivity of the evanescent field and, thus, the spatial relationship between the particles bound to the binding surface and the height of the evanescent field.

It is further preferred that the light detector is adapted to detect light being reflected from the binding surface. The sensing unit is preferentially adapted to generate the sensing signal based on frustrated total internal reflection (FTIR).

It is further preferred that the light detector is adapted to detect light being scattered from the particles bound on the binding surface.

The sensing unit preferentially comprises an objective lens for collecting the light of the evanescent field scattered by the bound particles on the binding surface, wherein the collected scattered light is imaged onto a two-dimensional light detector like a CCD or CMOS-camera by an imaging unit like an imaging lens. This allows using dark field microscopy (DFM) for generating a sensing signal. In particular, the sensing signal generated by DFM can be used to determine whether single beads are specifically or non-specifically bound to the binding surface.

The substance determination apparatus being preferentially a biosensor can comprise optical elements, wherein the substance determination apparatus preferentially further comprises means for correcting for achromatic effects caused by using different wavelengths. This means is, for example, an achromatic lens or a software tool which corrects for a shift between images of the binding surface on the light detector generated by different wavelengths, for example, if the light detector is a CCD detector.

It is further preferred that the sensing unit comprises a force applying unit for applying a force to the particles bound to the binding surface, wherein the sensing unit is adapted to modify at least one of i) the distance between the particles bound on the binding surface and the binding surface and ii) the in-plane position of the particles bound on the binding surface by modifying the force applied to the particles bound on the binding surface.

It should be noted that a modification of an in-plane position does not mean that the particles do have to be located directly on the binding surface. The bound particles can of course also be located with a distance to the binding surface. The in-plane position can be defined as the position of a particle orthogonally, i.e. orthogonal to the binding surface, projected onto the binding surface.

It is further preferred that the force applying unit is adapted to move the particles towards the binding surface and to move the particles in a direction away from the binding surface, wherein the sensing unit is adapted to generate a first sensing signal if the particles bound to the binding surface have been moved towards the binding surface and to generate a second sensing signal if the particles bound to the binding surface haven been moved in a direction away from the binding surface.

Different kinds of binding have generally different binding lengths. In particular, non-specifically bound particles have generally another binding length than specifically bound particles. If the particles are moved to the binding surface, the differences between the distances between different kinds of binding are rather smaller or not present at all. If the particles are moved in a direction away from the binding surface, the differences between the distances of the particles which are differently bound are increased, in particular, maximized. The deviations of the first and second sensing signals are therefore also increased, in particular, maximized, and can therefore be used to improve the quality of discriminating between different kinds of binding, in particular, to improve the quality of determining specifically bound particles.

It is further preferred that the sensing unit is adapted to generate several sensing signals over time while the particles bound to the binding surface are moved in a direction away from the binding surface, wherein the binding discrimination unit is adapted to discriminate between different kinds of binding depending on the several sensing signals generated over time.

In particular, the binding discrimination unit is preferentially a specific binding determination unit being adapted to determine the specifically bound particles depending on the several sensing signals generated over time.

If there are several kinds of non-specific bindings having different binding lengths and/or binding strength, and/or if there are different kinds of specific bindings having different binding lengths and/or binding strengths, the different kinds of particles having different binding lengths and/or strength reach their maximum excursion from the binding surface at different times. This reaching of a maximum excursion from the binding surface for a certain kind of particles is visible in the several sensing signals measured over time, which can also be regarded as a single time dependent sensing signal. The several sensing signals measured over time can therefore be used to distinguish between different kinds of specifically and/or non-specifically bound particles.

Over time the sensing signal, in particular, the total response from a FTIR sensing signal, will start at a minimal value when all particles are attracted to the binding surface and increases when the particles are moved away from the binding surface. The increase will flatten off in discrete steps as more particles are reaching their maximum height with respect to the binding surface given by their respective binding length. The discrete steps indicate the populations of the different kinds of binding, in particular, of specifically and non-specifically bound particles. The sensing signal measured over time, in particular, the discrete steps in the sensing signal, is therefore indicate of the population, in particular, the amount or concentration, of the particles bound by a certain kind of binding. The binding discrimination unit is therefore preferentially adapted to discriminate between different kinds of binding, in particular, to determine specifically bound particles, depending on the sensing signal measured over time, in particular, depending on the discrete steps in the sensing signal measured over time.

Since, while the several sensing signals are generated over time, the height of the particles changes gradually, the several sensing signals generated over time can be regarded as several first and second sensing signals.

The force applying unit is preferentially a magnetic unit for applying magnetic forces to the particles bound to the binding surface. The particles are preferentially particles which can be forced by a magnetic field. The magnetic unit can be adapted such that the particles can be attracted towards the binding surface or pulled away from the binding surface. The magnetic unit can also be adapted to modify the in-plane position of the bound particles, i.e. to move the particles in a lateral direction parallel to the binding surface. Moreover, the magnetic unit can be adapted such that the orientation of the particles, which are preferentially magnetic particles, can be modified. The orientation is preferentially changed such that the distance between the particles bound to the binding surface and the binding surface is modified.

In addition to or in an alternative, the force applying unit can be adapted to apply another force to the particles for modifying the distance between the particles bound to the binding surface and the binding surface and/or the in-plane position of the particles bound on the binding surface. For example, the force applying unit can be adapted to apply fluidic, electrostatic, sonic, etcetera, forces to the particles bound to the binding surface. In particular, the ionic content of the fluid can be modified for modifying the distance of the particles bound to the binding surface and the binding surface.

It is further preferred that the binding discrimination unit is adapted to discriminate between different kinds of binding depending on a ratio of the first sensing signal and the second sensing signal. In particular, the binding discrimination unit is a specific binding determination unit being adapted to determine the specifically bound particles depending on a ratio of the first sensing signal and the second sensing signal.

Since the first signal and the second signal depend in the same manner on the number of particles on the binding surface, but differently on the spatial relationship between the evanescent field and the particles bound to the binding surface, the ratio of these signals is indicative of this spatial relationship and, thus, of the distance and therefore of specific and non-specific binding.

It is further preferred that the substance determining apparatus further comprises:

a specific ratio providing unit (40) for providing a specific ratio being the ratio of i) one of the first sensing signal and the second sensing signal and ii) the other of the first sensing signal and the second sensing signal, indicative of a specific binding of the particles on the binding surface, a non-specific ratio providing unit (41) for providing a non-specific ratio being the ratio of i) one of the first sensing signal and the second sensing signal and ii) the other of the first sensing signal and the second sensing signal, indicative of a non-specific binding of the particles on the binding surface, wherein the specific binding determination unit is adapted to determine the amount of specifically bound particles as the ratio of a) the difference between i) the one of the first sensing signal and the second sensing signal and ii) the product of the non-specific ratio and the other of the first sensing signal and the second sensing signal, and b) the difference between i) one and ii) the ratio of the non-specific ratio and the specific ratio.

The specific ratio providing unit and the non-specific ratio providing unit are preferentially storing units, in which the specific ratio and the non-specific ratio are stored and from which these ratios can be retrieved. The specific ratio can be determined, for example, by generating the first sensing signal and the second signal, while a very high substance concentration is present in the fluid, i.e. preferentially a concentration at which the binding surface is saturated, i.e. completely occupied. Moreover, the non-specific ratio can be determined by generating a first sensing signal and a second sensing signal, while the substance is not present in the fluid.

This allows determining the amount of particles on the binding surface, which are specifically bound, with a high sensitivity.

The substance determination apparatus preferentially comprises a binding device, in particular, a cartridge, including the particles and the binding surface and being adapted to receive the fluid, and an analyzing device, which can be regarded as a reader, including the sensing unit and the specific binding determination unit.

The binding device is preferentially a disposable device and the analyzing device is preferentially a reusable device. Thus, by distributing the functionalities over the binding device and the analyzing device, a part of the substance determination apparatus can be used as a disposable device and the other part can be used as a reusable device. Since the fluid, which is preferentially a sample of a bodily fluid like blood, saliva or urine, is introduced into the binding device and since the binding device is a disposable device, the binding device can be used only one time before being disposed, i.e. a determination of specifically bound particles is not affected by impurities of a previous measurement.

In a first aspect of the present invention a binding device for cooperating with an analyzing device for determining a substance within a fluid is presented, wherein the binding device comprises
    particles for being attached to the substance within the fluid,
    a binding surface for binding the particles, if the particles have been attached to the substance,
    the analyzing device comprising:
    a sensing unit for sensing the particles on the binding surface, wherein the sensing unit is adapted to generate a sensing signal being indicative of at least one of i) a distance between the particles bound on the binding surface and the binding surface and ii) an in-plane position of the particles bound on the binding surface,
    a binding discrimination unit for discriminating between different kinds of binding of the particles bound on the binding surface depending on the generated sensing signal.

In a further aspect of the present invention an analyzing device for cooperating with a binding device for determining a substance within a fluid is presented, wherein the binding device comprises:
    particles for being attached to the substance within the fluid,
    a binding surface for binding the particles, if the particles have been attached to the substance,
    the analyzing device comprising:
    a sensing unit for sensing the particles on the binding surface, wherein the sensing unit is adapted to generate a sensing signal being indicative of at least one of i) a distance between the particles bound on the binding surface and the binding surface and ii) an in-plane position of the particles bound on the binding surface,
    a binding discrimination unit for discriminating between different kinds of binding of the particles bound on the binding surface depending on the generated sensing signal.

The analyzing device preferentially comprises a magnetic unit for attracting the particles, which are preferentially magnetic, to the binding surface.

In another example the magnetic unit is designed to generate a rotating magnetic field for applying a force to the particles, as for instance described in the publications WO2009/037636-A1 or WO2010/026551-A1.

In a further aspect of the present invention a substance determining method for determining a substance within a fluid is presented, wherein the substance determining method comprises following steps:
    attaching particles to the substance within the fluid,
    binding the particles to a binding surface, if the particles have been attached to the substance,
    sensing the particles on the binding surface, wherein a sensing signal is generated being indicative of at least one of i) a distance between the particles bound on the binding surface and the binding surface and ii) an in-plane position of the particles bound on the binding surface,
    discriminating between different kinds of binding of the particles bound on the binding surface depending on the generated sensing signal.

In a further aspect of the present invention a binding method for cooperating with an analyzing method for determining a substance within a fluid is presented, the binding method comprising following steps:
    attaching particles to the substance within the fluid,
    binding the particles to a binding surface, if the particles have been attached to the substance, the analyzing method comprising following steps:
    sensing the particles on the binding surface, wherein a sensing signal is generated being indicative of at least one of i) a distance between the particles bound on the binding surface and the binding surface and ii) an in-plane position of the particles bound on the binding surface,
    discriminating between different kinds of binding of the particles bound on the binding surface depending on the generated sensing signal, in particular, determining specifically bound particles being particles bound to the binding surface, which have been attached to the substance, depending on the generated sensing signal.

In a further aspect of the present invention an analyzing method for cooperating with a binding method for determining a substance within a fluid is presented, wherein the binding method comprises following steps:
    attaching particles to the substance within the fluid,
    binding the particles to a binding surface, if the particles have been attached to the substance, the analyzing method comprising following steps:
    sensing the particles on the binding surface, wherein a sensing signal is generated being indicative of at least one of i) a distance between the particles bound on the binding surface and the binding surface and ii) an in-plane position of the particles bound on the binding surface,
    discriminating between different kinds of binding of the particles bound on the binding surface depending on the generated sensing signal, in particular, determining specifically bound particles being particles bound to the binding surface, which have been attached to the substance, depending on the generated sensing signal.

These and other aspects of the invention will be apparent from and elucidated with reference to the embodiments described hereinafter.

BRIEF DESCRIPTION OF THE DRAWINGS

In the following drawings:

FIG. 1 shows schematically and exemplarily a cross-section of a binding device,

FIG. 2 shows schematically and exemplarily a capillary structure of the binding device, FIG. 3 shows schematically and exemplarily a top view on the binding device.

DETAILED DESCRIPTION OF EMBODIMENTS

Figure 4:
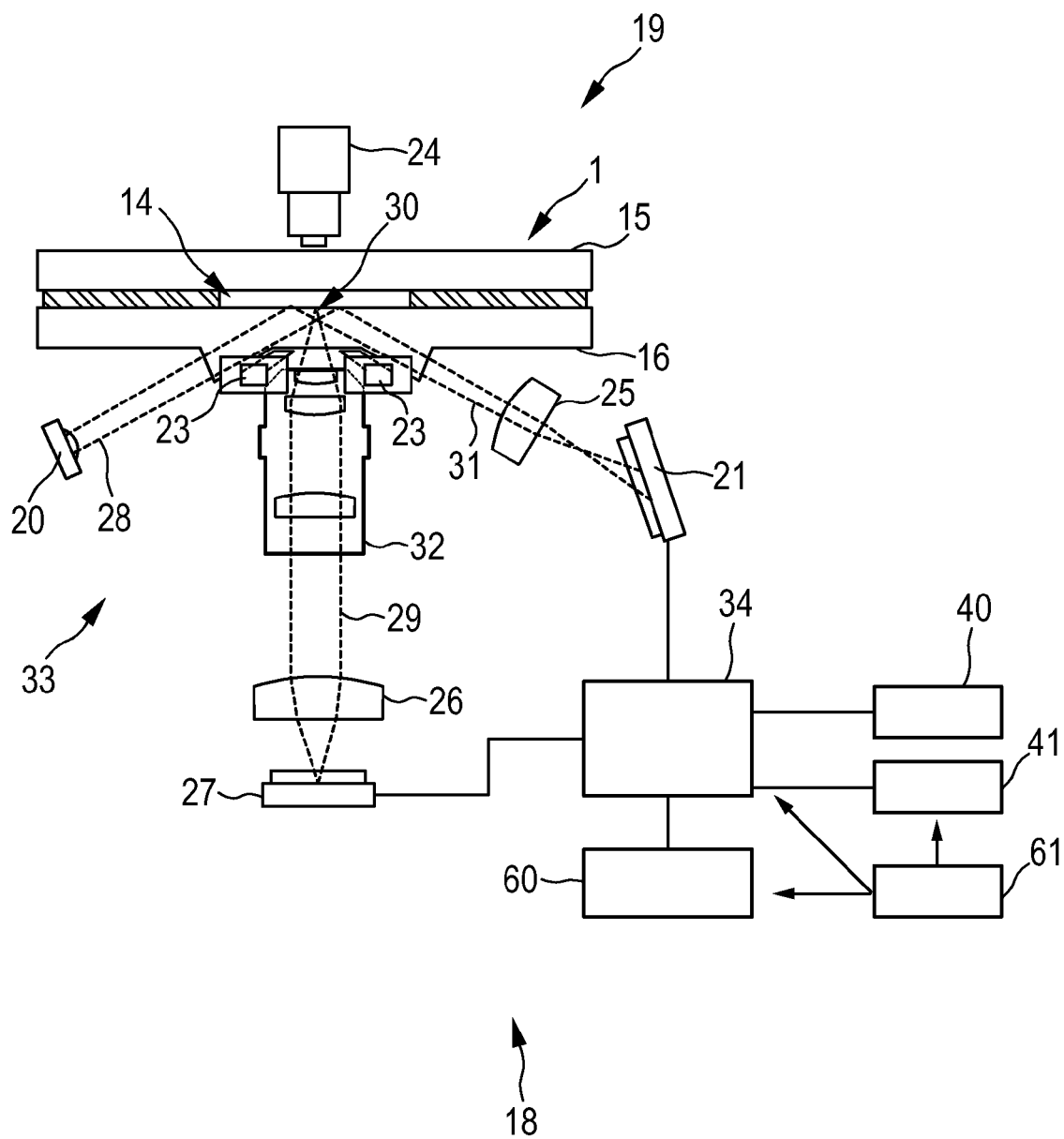
FIG. 4 shows schematically and exemplarily a substance determining apparatus comprising the binding device and an analyzing device.

FIG. 1 shows schematically and exemplarily a binding device 1 for binding a substance, which has to be determined within a fluid 3. The binding device 1 comprises a filter element 2 for filtering the fluid 3 and a capillary structure 5 for generating capillary forces. The capillary structure 5 is attached to the filter element 2 by using preferentially an adhesive. The capillary structure 5 is, in this embodiment, made of a double-sided tape which is adhesive on two sides.

The binding device 1 comprises a filtering location 6 at which the filter 2 is located and a sensing location 7 at which a substance within the fluid 3 is detectable, wherein the capillary structure 5 is formed such that the filtered fluid 3 is guided from the filtering location 6 to the sensing location 7 by capillary forces.

The capillary structure 5 comprises a collecting channel, which connects the filtering location 6 with the detection location 7, and guiding channels 9 located at the filtering location 6, wherein the guiding channels 9 extend from an end of the connecting channel 8. In this embodiment the guiding channels 9 extend radially from the end 10 of the connecting channel 8. The capillary structure 5 is schematically and exemplarily shown in more detail in FIG. 2. FIG. 3 shows schematically and exemplarily a top view on the binding device 1 which is shown in a sectional view in FIG. 1.

The binding device 1 comprises a sensing cavity 14 which is located at the sensing location 7 and in which a substance of the fluid 3 is detectable. This sensing cavity 14 is formed by a first part 15 and a second part 16 of the binding device 1 together with the capillary structure 5. In addition, the first part 15 and the second part 16 form together with the capillary structure 5 the connecting channel 8. The first part 15 and the second part 16 are preferentially attached to each other via an adhesive, in particular, via the double-sided tape forming the capillary structure 5. The first part 15 and the second part 16 are plastics substrates which are injection molded and preferentially transparent to visible light. The first part 15 can be regarded as an upper substrate or a closing element or cover element and the second part 16 can be regarded as a lower substrate or a base element of the binding device 1. The first part 15 comprises a vent 22 for allowing a gas to leave the capillary structure 5.

In this embodiment, the filter element 2 is a blood separation filter and the binding device 1 forms a cartridge which is preferentially disposable. The binding device 1 is preferentially used in point-of-care diagnostics. The binding device 1 is preferentially adapted for detecting a low concentration bio marker in a sample of whole blood, in particular, in a finger prick sample of, for example, 25 μl. The sensing location 7 preferentially comprises an immunoassay. In particular, the sensing location 7 comprises a group 17 of particles for being attached to a substance within the fluid 3, wherein the group of particles mixes with the fluid 3, and the particles attach the substance within the fluid 3, if the fluid 3 is at the sensing location 7. The group 17 of particles can also be located between the sensing location 7 and the filtering location 6.

FIG. 4 shows schematically and exemplarily a substance determining apparatus 19 comprising the binding device 1 and an analyzing device 18. The binding device 1 has been inserted into the analyzing device 18. The analyzing device 18 comprises a sensing unit 33 for sensing the particles on the binding surface 30, wherein the sensing unit 33 is adapted to generate a sensing signal being indicative of a distance between the particles bound on the binding surface 30 and the binding surface 30. The analyzing device 18 further comprises a binding discrimination unit 34 for discriminating between different kinds of binding of the particles bound on the binding surface depending on the generated sensing signal. In this embodiment, the binding discrimination unit 34 is a specific binding determination unit 34 for determining specifically bound particles being particles bound to the binding surface 30, which have been attached to the substance, depending on the generated sensing signal. The substance determining apparatus 19 is a magnetic biosensor, wherein the particles are magnetic beads, i.e. nanoparticles, which label the substance by being attached to the substance. For attaching the substance the magnetic beads are functionalized with an attaching element that can be attached to the substance being, for example, a specific analyte molecule. In this embodiment, the attaching element is an antibody. However, the attaching element can also be a protein, DNA, aptamer et cetera.

The analyzing device 18 comprises a magnetic unit 23, 24 for attracting the magnetic particles to the binding surface 30 and for pulling the magnetic particles away from the binding surface 30. The magnetic unit comprises a horseshoe magnet 23 being preferentially in a planar arrangement at one side of the binding device 1, if the binding device is inserted into the analyzing device, and a second magnet 24 being arranged on the opposite side of the binding device 1, if the binding device is inserted into the analyzing device. The magnetic unit 23, 24 is a force applying unit for applying a force to the particles bound to the binding surface 30.

The sensing unit 33 further comprises a light source 20 being, for example, a light emitting diode or a laser for generating radiation 28 for being directed to the binding surface 30 for generating an evanescent field on the binding surface 30.

The evanescent field on the binding surface 30 is influenced by the particles bound to the binding surface 30, thereby influencing a reflected light beam 31 comprising the light being total internally reflected at the cartridge surface, and a scattered light beam 29 comprising the light of the evanescent field scattered by the particles bound to the binding surface 30. The reflected light 31 is imaged by an objective 25 onto a first light detector 21 being preferentially a CCD camera. The scattered radiation is collected by a microscope objective 32 and imaged on a second detector 27 by an imaging lens 26. The first detector 21 and the second detector 27 generate sensing signals which are provided to the specific binding determination unit 34 for determining specifically bound particles being particles bound to the binding surface 30, which have been attached to the substance, depending on the generated sensing signals. The sensing signal of the first detector 21 is based on FTIR and the sensing signal generated by the second detector 27 is based on DFM. The specific binding determination unit 34 is preferentially adapted to determine the amount of specifically bound particles on the binding surface 30.

In the following the generation of FTIR sensing signals will be shortly described. If a beam of light reflects on the interface between a medium with a higher refractive index, for example the second part 16, and a lower refractive index, for example the fluid, there is a certain critical angle of incidence above which there is a situation of total internal reflection (TIR). The detection configuration (regarding refractive indices and angle of incidence) shown in FIG. 4 is such that there is total internal reflection of the incoming beam. Although the light is totally reflected in such a situation, there is still penetration of the light in a very thin layer of the medium with the low refractive index. This is called an evanescent field, the intensity of which decays exponentially in the low refractive index medium with a characteristic penetration depth of the order of the wavelength of the light. So, in practice the penetration depth is preferentially less than 0.5 micrometer. If magnetic particles are bound to the binding surface 30, the optical properties of this very thin first fluid layer of preferentially about 0.5 micrometer are changed leading to a reduction of the intensity of the reflected light beam. This is caused by absorption and scattering of the evanescent light (FTIR; frustrated total internal reflection). As a result the light intensity, and hence the signal, at the detector 21 decreases, whereas the light intensity, and hence the signal, at the detector 27 increases.

For completeness, in the following examples of optical methods are disclosed, e.g. a dark field detection with a spatial filtering (not shown) in the second detector 27 that is additionally arranged in the path of the reflected light beam 31 between the cartridge 1 and the second detector 27. A clear advantage of the FTIR detection method is the use of well-collimated parallel incoming beam illuminating the binding surface 30, and hitting the second detector 27 after reflection. When using an imaging (convergent) lens in the second detector 27 of the detection branch, virtually all the totally internally reflected light of the reflected light beam 31 is going through the focal plane of the lens and (depending on the NA of the lens and the wavelength of the light) is concentrated in a very small area in the focal plane (Fourier plane) of the imaging lens. In one example, the light further propagates towards the image plane hitting the second detector 27 and generating there a bright-field image of the binding surface 30. According to a different example, a spatial filter (obstruction mask, not shown) is however positioned in the Fourier plane of the imaging lens with a dimension slightly larger than the focused spot. This has the effect that all light stemming from total internal reflection will be blocked by the obstruction and none of this light is hitting the detector 27, resulting in a zero optical signal (i.e. dark image) when no scattering takes place at the binding surface 30.

When a binding of target particles takes place at the binding surface 30, scattering of light results in light being scattered in random directions, other than the direction of the main reflected outgoing light beam 31. Consequently, these scattered rays will pass the Fourier plane of the lens off-axis, and will not be blocked by the on-axis obstruction of a filter for dark field imaging, resulting in some light on the second detector 27. Since the scattered light is still imaged onto the second detector 27, the measured signal is now directly proportional to the amount of scattering, which is proportional to the amount of bound target particles. In this way one obtains an optical 'x-signal', which can be processed further by the devices described above with a high SNR.

Figure 5:
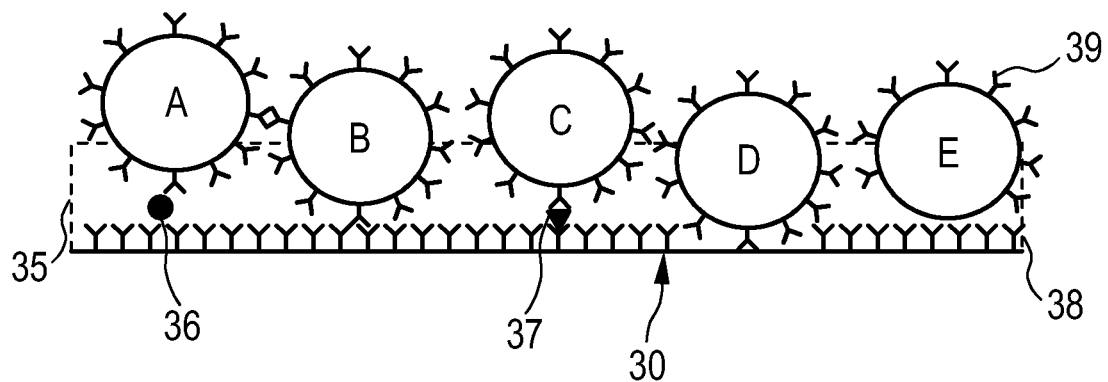
FIG. 5 shows schematically and exemplarily different kinds of binding to a binding surface.

FIG. 5 shows schematically and exemplarily different kinds of binding on the binding surface 30. In FIG. 5 the broken line 35 indicates schematically and exemplarily a height of the evanescent field which can be defined as a decay length $\zeta$ of the evanescent field. Since the evanescent field decreases exponentially with increasing distance to the binding surface 30, a particle being closer to the binding surface has a larger influence on the evanescent field than a particle being more far away from the binding surface 30. The particle indicated by A is specifically bound to the binding surface 30 via the attaching element 39, the substance 36 and the binding element 38. The particle B does not form a normal sandwich like the particle A, but is bound to the binding surface 30 via the attaching element 39 and the binding element 38, i.e. without a sandwiched substance.

The particle C is bound to the binding surface 30 via the attaching element 39, an element 37 not being the substance to be determined, i.e. not being the analyte, and the binding element 38. The particle D is directly bound to an exposed area on the binding surface 30 via the attaching element 39. This means, the binding surface 30 comprises the binding elements 38 for forming a normal sandwich as shown in FIG. 5 for the particle A. These binding elements 38 also bind particles B, C and E in the example shown in FIG. 5. However, the particle D is directly bound to the binding surface 30 via the attaching element 39.

An exposed area of the particle E is bound to the binding surface 30 directly via the binding elements 38, i.e. the particles comprise attaching elements 39 for attaching the substance, wherein the particles A, B, C, D are bound to the binding surface 30 via the attaching elements 39 of the respective particle. However, the particle E is not bound to the binding surface 30 via the attaching elements 39, but an exposed area of the particle E is attached to the binding surface 30 via the binding element 38.

In FIG. 5, only the particle A forms a normal sandwich. The particle A is therefore specifically bound to the binding surface 30. The other particles B, C, D, E do not form a normal sandwich and are therefore non-specifically bound to the binding surface 30. As can be seen in FIG. 5, the distance of the specifically bound particle A differs from the distances of the non-specifically bound particles B, C, D, E to the binding surface 30.

A non-specific binding is preferably any binding that is not dependent on the presence of the substance, i.e. on the presence of the specific analyte that is to detect in the sample fluid. FIG. 5 illustrates differences between specific and non-specific binding for a sandwich immunoassay. However, also other kinds of assay can comprise specific and non-specific binding and the substance determining apparatus 19 can also be used to determine specifically bound particles if another assay is chosen for determining the substance in the fluid.

The sensing unit 33 is adapted to modify the spatial relationship between the evanescent field and the particles bound to the binding surface 30, to generate a first sensing signal depending on a first spatial relationship between the evanescent field and the particles bound to the binding surface 30, and to generate a second sensing signal depending on a second spatial relationship between the evanescent field and the particles bound to the binding surface 30, wherein the specific binding determination unit 34 is adapted to determine the specifically bound particles depending on the first sensing signal and the second sensing signal. The first sensing signal and the second sensing signal can be FTIR signals generated by the first detector 21. However, the first sensing signal and the second sensing signal can also be DFM signals generated by the second detector 27. Moreover, the specific binding determination unit 34 can be adapted to determine the specifically bound particles depending on first and second FTIR signals generated by the first detector 21 and on first and second DFM sensing signals generated by the second detector 27.

Preferentially, the sensing unit 33 is adapted to sense the particles on the binding surface 30 by generating a first evanescent field having a first dependency on the distance from the binding surface 30 and a second evanescent field having a second dependency on the distance from the binding surface 30 and to generate the first signal depending on an influence on the first evanescent field by the particles and the second signal depending on an influence of on second evanescent field by the particles.

Since the two evanescent fields have different dependencies on the distance from the binding surface 30, influences of the different evanescent fields by the particles on the binding surface 30 are indicative of particles located at different distances to the binding surface 30. Since specific and non-specific binding are generally different with respect to the distance to the binding surface 30, the first sensing signal and second sensing signal can be used for determining specifically bound particles.

In this embodiment, the sensing unit 33 is adapted to modify the relationship between the evanescent field and the particles bound to the binding surface 30 by modifying the wavelength of the radiation 28 being directed to the binding surface 30. In particular, the light source 20 is adapted to generate first radiation having a first wavelength for being directed to the binding surface 30 and for generating a first evanescent field and second radiation having a second wavelength for being directed to the binding surface 30 and for generating a second evanescent field, wherein the light detectors 21, 27 are adapted to detect the first radiation and the second radiation after having been reflected and scattered, respectively, at the binding surface, wherein the light detectors 21, 27 are adapted to generate the first sensing signal depending on the detected first radiation and to generate the second sensing signal depending on the detected second radiation.

The light detectors 21, 27 are preferentially adapted to distinguish the first wavelength and the second wavelength. Alternatively or in addition, the sensing unit 33 can be adapted to illuminate the binding surface 30 first with the first radiation and then with the second radiation or vice versa. In this case, the light detectors 21, 27 do not need to distinguish between the first wavelength and the second wavelength.

The light source 20 can comprise two light emitting diodes or two lasers for generating different wavelengths. In particular, the light source 20 preferentially comprises a red light emitting diode and a blue light emitting diode. In another embodiment, the first evanescent field and the second evanescent field can be generated by modifying the angle under which the radiation meets the binding surface 30.

As can be seen in FIG. 5, the distance between the binding surface 30 and the particles is in the case of non-specific binding often not the same as in the case of specific binding. For example, only the distance of the non-specifically bound particle C to the binding surface 30 may be close to the distance of the specifically bound particle A to the binding surface 30. For the further non-specifically bound particles B, D, E the differences with respect to the distances to the binding surface 30 are more pronounced. Since specific and non-specific binding generally differs in distance to the binding surface and since the sensing unit 33 generates sensing signals being indicative of a distance between the particles bound on the binding surface 30 and the binding surface 30, the specific binding determination unit 34 can determine specifically bound particles depending on the generated sensing signals.

The sensing signal is preferentially a signal change which depends on the number of particles on the binding surface and the signal change per particle in accordance with following equation:

$$S=Ns, \tag{1}$$

wherein S indicates the signal change, i.e. the sensing signal, N indicates the number of particles on the binding surface 30 within the evanescent field and s indicates the signal change per particle. The signal change per particle is dependent on the distance of the particles from the binding surface 30. Assuming that there are two levels, the signal change can be defined as:

$$S=N_s s_s + N_a s_a, \tag{2}$$

wherein $N_s$ indicates the number of specifically bound particles within the evanescent field on the binding surface 30, $s_s$ indicates the signal change per specifically bound particle, $N_a$ indicates the number of non-specifically bound particles within the evanescent field on the binding surface 30, and $s_a$ indicates the signal change per non-specifically bound particle.

If a first sensing signal has been generated while a first evanescent field was present and if a second sensing signal has been generated while a second evanescent field was present, the first sensing signal and the second sensing signal depend in the same manner on the number of particles within the same region of interest, but differently on the distance of the particles from the binding surface 30. The ratio of the first sensing signal and the second sensing signal is therefore indicative of the distance of the particles from the binding surface 30.

In particular, particles having the same distance to the binding surface lead to the same ratio of the first and second sensing signals, even if the amount of particles on the binding surface is different. The specific binding determination unit 34 is therefore adapted to determine the specifically bound particles depending on the ratio of the first sensing signal and the second sensing signal.

The first sensing signal $S^R$ and the second sensing signal $S^B$ can be defined by following equations:

$$S^R=N_s s_s^R + N_a s_a^R \text{ and} \tag{3}$$

$$S^B=N_s s_s^B + N_a s_a^B, \tag{4}$$

wherein the superscripts $^R$ and $^B$ are used to distinguish the sensing signals, i.e. the signal changes, and signal changes per particle for the measurement for generating the first sensing signal and the measurement for generating the second sensing signal, in particular, for distinguishing the two measurements performed by red light and blue light, respectively, or performed by entrance angles θ1 and θ2, respectively.

The specific binding determination unit 34 is preferentially adapted to determine $N_s s_s^R$ or $N_s s_s^B$, i.e. the specific binding determination unit 34 is preferentially adapted to subtract the contribution of the non-specific binding from the sensing signal. The result is then a sensing signal, in particular, a signal change, caused by specifically bound particles only. This signal can directly be used for, for example, determining the amount of specifically bound particles on the binding surface 30. For example, the substance determining apparatus 19 can be calibrated by determining the sensing signal, from which the contribution of the non-specific binding has been subtracted, while known amounts of specifically bound particles are present on the binding surface.

In an embodiment, the sensing unit 33 is adapted such that sensing signals, i.e. signal changes, caused by single particles can be distinguished using the scattered light 29 collected by the microscope objective 32 and imaged onto the second light detector 27 by the imaging lens 26. In this embodiment, the second light detector 27 comprises preferentially a two-dimensional detection surface, wherein different locations on the two-dimensional detection surface correspond to sensing signals of different particles on the binding surface 30. Thus, for single particles bound to the binding surface 30 first and second sensing signals can be generated. For each particle the ratio of the first sensing signal and the second sensing signal can be determined and this ratio can be used by the specific binding determination unit 34 for determining for each single particle, if the respective particle is specifically or non-specifically bound to the binding surface.

Moreover, the image detected by the second light detector 27 can also be used to just count the number of particles bound to the binding surface 30. Moreover, a first FTIR sensing signal and a second FTIR sensing signal can be generated by the first light detector 21. The first sensing signal is the signal change during a first measurement, for example, while using a first wavelength, and the second sensing signal is a signal change measured during a second measurement, for example, while using a second wavelength. Since the signal change and the number of particles have been measured, the signal change per particle $s_s^R$, $s_a^R$, $s_s^B$, $s_a^B$ can be determined and be used for solving equations (3) and (4). In this way, the specific binding determination unit can determine the number of specifically bound particles $N_s$ and the number of non-specifically bound particles $N_a$.

The embodiment of the substance determining apparatus 19 schematically and exemplarily shown in FIG. 4 preferentially further comprises a specific ratio providing unit 40 for providing a specific ratio being the ratio of the first sensing signal and the second signal and being indicative of a specific binding of the particles on the binding surface 30, and a non-specific ratio providing unit 41 for providing a non-specific ratio being the ratio of the first sensing signal and the second sensing signal and being indicative of a non-specific binding of the particles on the binding surface. In this embodiment, the specific ratio providing unit 40 and the non-specific ratio providing unit 41 are storing units in which the specific ratio and the non-specific ratio are stored and from which these ratios can be retrieved. The specific ratio can be determined, for example, by generating the first sensing signal and the second sensing signal, while a very high substance concentration is present in the fluid, i.e. preferentially a concentration at which the binding surface 30 is saturated, i.e. completely occupied. The specific ratio is therefore a ratio between a first sensing signal and a second sensing signal, wherein the first sensing signal and the second sensing signal are caused by specifically bound particles only. The non-specific ratio can be determined by generating a first sensing signal and a second sensing signal, while the substance is not present at all in the fluid. Thus, the non-specific ratio is a ratio between the first sensing signal and the second sensing signal, wherein the first sensing signal and the second signal are not generated by specifically bound particles, but substantially only by non-specifically bound particles. The specific ratio $Q_s$ and the non-specific ratio $Q_a$ do not depend on the number of specifically or non-specifically bound particles and can be described by following equations:

$$Q_s = \frac{S^R}{S^B} = \frac{N_s s_s^R}{N_s s_s^B} = \frac{s_s^R}{s_s^B} \tag{5}$$

and $$Q_a = \frac{S^R}{S^B} = \frac{N_a s_a^R}{N_s s_s^B} = \frac{s_s^R}{s_s^B} \tag{6}$$

Using equations (5) and (6), equation (4) can be rewritten as:

$$S^B = N_a \frac{s_a^R}{Q_a} + N_s \frac{s_s^R}{Q_s}, \tag{7}$$

which can be rearranged as:

$$N_a s_a^R = Q_a \left( S^B - N_s \frac{s_s^R}{Q_s} \right). \tag{8}$$

Equation (8) can be combined with equation (3) to yield:

$$S^R = N_s s_s^R + Q_a S^B - N_s s_s^R - N_s s_s^R \frac{Q_a}{Q_s}, \tag{9}$$

which can be rearranged as:

$$N_s s_s^R = \frac{S^R - Q_a S^B}{1 - \frac{Q_a}{Q_s}}. \tag{10}$$

In accordance with the equation (10), the specific binding determination unit is adapted to determine the part of the sensing signal, which is caused by specifically bound particles, as the ratio of a) the difference between i) the first sensing signal and ii) the product of the non-specific ratio and the second sensing signal, and b) the difference between i) one and ii) the ratio of the non-specific ratio and the specific ratio.

As already mentioned above, the specific binding determination unit 34 can be adapted to determine the amount of specifically bound particles depending on $N_s s_s^R$ or $N_s s_s^B$.

The specific binding determination unit 34 is preferentially adapted to determine specifically bound particles based on equation (10) from first and second FTIR sensing signals generated by the first light detector 21. However, the specific binding determination unit 34 can also be adapted to determine the amount of specifically bound particles based on equation (10) and first and second DFM sensing signals generated by the second light detector 27.

The determination of the specifically bound particles, in particular, the part of the sensing signal generated by the specifically bound particles, described above with reference to equations (1) to (10), can also be used if the first sensing signal and the second sensing signal are determined in another way, as long as the first sensing signal has been generated depending on at least one of i) a first distance between the particles bound to the binding surface and the binding surface, ii) a first in-plane position of the bound particles on the binding surface, and iii) a first distance sensitivity and the second sensing signal has been generated depending on at least one of i) a second distance between the particles bound to the binding surface and the binding surface, ii) a second in-plane position of the bound particles on the binding surface, and iii) a second distance sensitivity, wherein between generating the first sensing signal and generating the second sensing signal at least one of i) the distance between the particles bound to the binding surface and the binding surface, ii) the in-plane position of the bound particles on the binding surface and iii) the distance sensitivity of the sensing unit has been modified. For example, the first sensing signal can be generated while the particles bound to the binding surface have been moved towards the binding surface and/or in a first lateral direction, and the second sensing signal can be generated while the particles bound to the binding surface have been moved away from the binding surface and/or in a second lateral direction.

The determination of the specifically bound particles, in particular, the part of the signal generated by the specifically bound particles, described above with reference to equations (1) to (10), is based on the assumption that particles having the same distance to the binding surface lead to the same ratio of the first and second sensing signals. This assumption is very well fulfilled, if the diameter of the particles does not vary too much. If the diameter of the particles is considered, following equations describe the mentioned ratio, if the first signal is generated by using a first wavelength and if the second sensing signal is generated while using a second wavelength being different to the first wavelength:

$$R_1 = \frac{\sigma(d_1, \lambda^R)}{\sigma(d_1, \lambda^B)} \cdot \exp[-z/(\zeta(\lambda^R) - \zeta(\lambda^B))] \quad (11)$$

and $$R_2 = \frac{\sigma(d_2, \lambda^R)}{\sigma(d_2, \lambda^B)} \cdot \exp[-z/(\zeta(\lambda^R) - \zeta(\lambda^B))], \quad (12)$$

wherein $d_1$ indicates the diameter and $R_1$ indicates the ratio of the first sensing signal and the second sensing signal of a first particle, wherein $d_2$ indicates the diameter and $R_2$ indicates the ratio of the first sensing signal and the second sensing signal of a second particle, $\lambda^{R,B}$ indicates the first and second wavelengths, respectively, z indicates the distance of the particle to the binding surface, $\zeta$ indicates the decay length of the evanescent field, and $\sigma$ indicates the cross section.

If the first sensing signal and the second sensing signal are generated using different entrance angles $\theta^{R,B}$, instead of wavelength multiplexing, the ratios of the first sensing signal and the second sensing signal for a first particle and a second particle can be defined by following equations:

$$R_1 = \frac{\sigma(d_1, \lambda)}{\sigma(d_1, \lambda)} \cdot \exp[-z/(\zeta(\theta^R) - \zeta(\theta^B))] \quad (13)$$

and $$R_2 = \frac{\sigma(d_2, \lambda^R)}{\sigma(d_2, \lambda^B)} \cdot \exp[-z/(\zeta(\theta^R) - \zeta(\theta^B))]. \quad (14)$$

The ratios are therefore, if entrance angle multiplexing is used, independently of the diameter of the particles. The combination of using a single or multiple wavelengths and multiple entrance angles $\theta$ can therefore help facilitating the data processing. For example, since the cross section $\sigma$ does not have a $\theta$-dependence, the cross section $\sigma$ can drop out from equations in the case of comparing two measurements at different entrance angles, but with fixed wavelength. The determination described above with reference to equations (1) to (10) can therefore also be used with high accuracy, if entrance angle multiplexing is used instead of wavelength multiplexing.

As an exemplarily embodiment, in the following a preferred sensing signal analysis will be described in more detail.

The amount of photons scattered and absorbed by a single bead with diameter d at wavelength $\lambda$ and height z above the optical interface, i.e. the binding surface, results in a drop of the FTIR signal equal to S:

$$S \approx \sigma(\lambda, d) \cdot e^{-\zeta(\lambda) \cdot z} \quad (15)$$

where $\sigma(\lambda, d)$ is the total ($4\pi$-integrated) scattering/absorption cross section of the bead with diameter d at wavelength $\lambda$, and $\zeta$ is the exponential decay constant of the evanescent field:

$$\zeta(\lambda) = \frac{4\pi \sqrt{n_1^2 \sin^2 \theta - n_2^2}}{\lambda}. \quad (16)$$

In the case of a FTIR sensing signal, a total (decrease of the) FTIR signal is the signal S integrated over the full ensemble of surface bounded beads, i.e. particles, having a certain bead diameter and height distribution. The bead diameter distribution is in principle a known function for a given batch of superparamagnetic beads, and can be written as $f(d)$ with $$\int_0^\infty f(x) \cdot dx = 1. \quad (17)$$

In the following we distinguish between specific and non-specific bound beads, with average bead heights $z_a^{avg}$ and $z_s^{avg}$. Furthermore we assume that there is no correlation between the distribution of bead heights and the bead diameter, i.e. for each bead diameter the distribution of the bead heights for a specific (or non-specific) bound bead is the same. These distributions are then given by $g_s(z)$ and $g_s(z)$ with $$\int_0^\infty g_{s(a)}(z) \cdot dz = N_{s(a)} \quad (18)$$

and

-continued $$z_{s(a)}^{avg} = \frac{\int_0^\infty z \cdot g_{s(a)}(z) \cdot dz}{\int_0^\infty g_{s(a)}(z) \cdot dz}. \quad (19)$$

The total FTIR signal at wavelength λ, integrated over the ensemble of beads can then be written as:

$$S_{tot}^\lambda \approx \int_0^\infty f(x) \cdot \left( \int_0^\infty g_s(z) \cdot \sigma(\lambda, x) \cdot e^{-\zeta(\lambda) \cdot z} \cdot dz + \int_0^\infty g_a(z) \cdot \sigma(\lambda, x) \cdot e^{-\zeta(\lambda) \cdot z} \cdot dz \right) \cdot dx == \int_0^\infty f(x) \cdot \sigma(\lambda, x) \cdot dx \cdot \int_0^\infty (g_s(z) + g_a(z)) \cdot e^{-\zeta(\lambda) \cdot z} \cdot dz \quad (20)$$

For a single well-defined bead diameter d (i.e. $f(x)=\delta(d)$), and a total of $N_{s(a)}$ (non-) specific bound beads with surface heights $z_{s(a)}$ this equation simplifies to:

$$S_{tot}^\lambda \approx \sigma(\lambda, d) \cdot (N_s \cdot e^{-\zeta(\lambda) \cdot z_s} + N_a \cdot e^{-\zeta(\lambda) \cdot z_a}). \quad (21)$$

If it is assumed that the cross sections σ(λ·d) are known for a certain batch of beads then basically four unknowns: $N_s, N_a, z_s$ and $z_a$ have to be determined. The experimentally obtained quantity $M_i$ can be defined as $$M_i = S_{tot}^{\lambda_i}/(\sigma(\lambda_i, d) \cdot \eta(\lambda_i)) \quad (22)$$

where $\eta_i$ accounts for the different detection efficiencies at different wavelengths. If the FTIR signal $S_{tot}^\lambda$ is measured at four different wavelengths, four equations of the form $$M_i = (N_s \cdot e^{-\zeta_i \cdot z_s} + N_a \cdot e^{-\zeta_i \cdot z_a}); i=1 \ldots 4 \quad (23)$$

are generated with basically four unknowns (assuming the cross sections σ(λ_i,d) are known). Consequently, from these four measurements the ratio of specific to non-specific beads is determined.

As an exemplarily embodiment, in the following some equations for height discrimination by using single bead detection will be described in more detail.

In the case of single bead imaging single binding events can be resolved individually and the detected signal $S_j$ corresponds to a single bead j only.

$$S_j \approx \sigma(\lambda, d_j) \cdot e^{-\zeta(\lambda) \cdot z_j} \quad (24)$$

Single beads are being imaged and processed. Basically for each bead we have two unknowns: diameter $d_j$ and height $z_j$. Now if the signal $S_j$ from bead j at two different wavelengths $\lambda_j$ is measured, information on bead height and diameter for each bead individually can be extracted by solving the following set of two equations:

$$S_j(\lambda_1)/\eta_1 \approx \sigma(\lambda_1, d_j) \cdot e^{-\zeta(\lambda_1) \cdot z_j}$$

$$S_j(\lambda_2)/\eta_2 \approx \sigma(\lambda_2, d_j) \cdot e^{-\zeta(\lambda_2) \cdot z_j} \quad (25)$$

In order to solve these equations the scattering/absorption cross section should be known as a function of wavelength and bead diameter. In the ideal case when this cross section can be written as a product like $$\sigma(\lambda_i, d_j) = \sigma^\lambda(\lambda_i) \cdot \sigma^d(d_j), \quad (26)$$

the bead diameter drops out of the equation and the bead height can be directly calculated:

$$z_j = \frac{1}{[\zeta(\lambda_2) - \zeta(\lambda_1)]} \cdot \ln\left[\frac{S_j(\lambda_1)}{S_j(\lambda_2)} \cdot \frac{\eta_2 \cdot \sigma^\lambda(\lambda_2)}{\eta_1 \cdot \sigma^\lambda(\lambda_1)}\right] + C(\lambda_1, \lambda_2) \quad (27)$$

with C being an offset value (determined by e.g. the excitation beam intensity), constant for a specific wavelength combination, and being the same for all beads that are being detected during a dual wavelength measurement.

From solving equation (27) for a large number of beads, the distribution functions $g_s(z)$ and $g_a(z)$ can be obtained, and from these the ratio $N_s/N_a$ can be derived.

As described above with reference to FIG. 4, the substance determining apparatus 19 comprises a magnetic unit 23, 24 being a force applying unit. Preferentially, the sensing unit 33 is adapted to modify the relationship between the evanescent field and the particles bound to the binding surface 30 by modifying the force applied to the particles bound to the binding surface 30. In particular, the sensing unit 33 is preferentially adapted to generate a first sensing signal if the particles bound to the binding surface are attracted towards the binding surface and to generate a second sensing signal if the particles bound to the binding surface are pulled in a direction away from the binding surface.

The sensing unit 33 is preferentially adapted to determine the average surface particle density and the average binding length based on FTIR sensing signals, wherein first sensing signals are generated while the particles are attracted to the binding surface 30 and second sensing signals are determined while the particles are pulled away from the binding surface 30. It should be noted that the attraction of the particles to the binding surface 30 can also be introduced by lateral oriented magnetic fields, wherein the particles turn over towards the binding surface 30.

As preferentially performed in all described embodiments, after the fluid has mixed with the particles for allowing the particles to attach the substance within the fluid, the particles are attracted to the binding surface for allowing the particles to be bound on the binding surface. Then, the particles which are not bound to the binding surface are pulled away from the binding surface. The last step can be regarded as a washing step.

In this embodiment, after the washing step the particles are attracted towards the binding surface 30 while using the magnetic unit. The FTIR sensing signal measured while the bound particles are attracted towards the binding surface 30 is indicative of the surface particle density.

Figure 6:
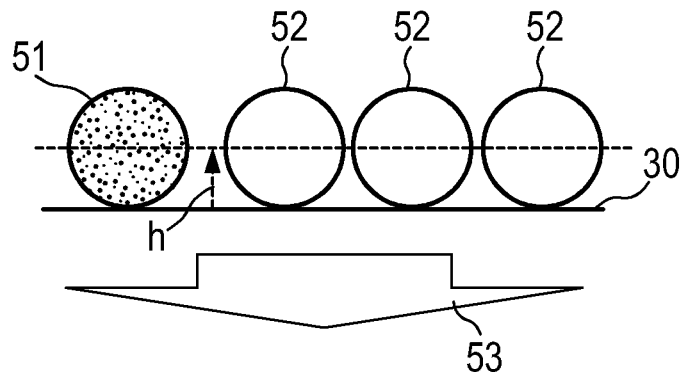
FIGS. 6-11 show schematically and exemplarily the influence of a force applied to particles bound to the binding surface.

FIG. 6 schematically and exemplarily shows the situation when the particles 51, 52 are attracted to the binding surface 30 by a force indicated by the arrow 53. The particle 51 is specifically bound and the particles 52 are non-specifically bound. The reference sign h indicates the average particle height with respect to the binding surface 30.

In a next step, bindings are gently stretched by attracting the particles 51, 52 upwards with respect to the binding surface 30. This is schematically and exemplarily shown in FIG. 8.

Figure 7:
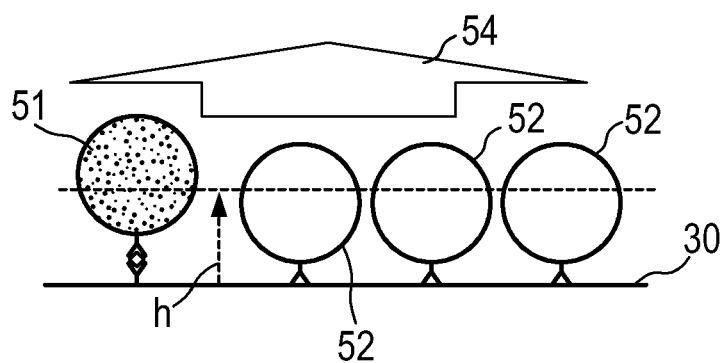

In FIG. 7, the bindings of the particles 51, 52 have been stretched by pulling the particles 51, 52 away from the binding surface 30 by applying a magnetic force indicated by the arrow 54. Since the particles are pulled away from the binding surface, the average bead height h is increased.

By varying the optical excitation conditions, for example, by measuring FTIR sensing signals with two wavelengths or with two different angles under which the light meets the binding surface 30, while the bindings of the particles 51, 52 are stretched, the average binding length can be determined. Combining the results of the measurements performed while the particles are attracted to the binding surface and while the particles are pulled away from the binding surface, allows calculating the fraction of non-specific bindings and to correct the FTIR sensing signal appropriately.

The sensing unit 33 is preferentially further adapted to generate several sensing signals over time, i.e. at different points in time a sensing signal or a time dependent sensing signal, while the particles bound to the binding surface are pulled in a direction away from the binding surface, wherein the specific binding determination unit 34 is adapted to determine the specifically bound particles depending on the several sensing signals generated over time. The generation of the time dependent sensing signal will in the following be exemplarily described with reference to FIGS. 8 to 11.

After the washing step, the particles are attracted towards the binding surface. The sensing signal generated in this situation is indicative of the particle bead density.

Figure 8:
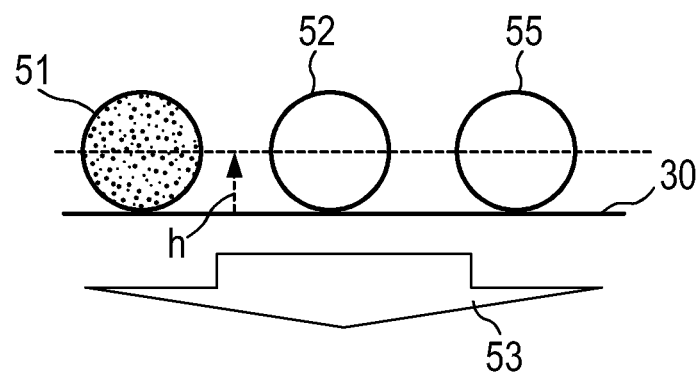
Figure 9:
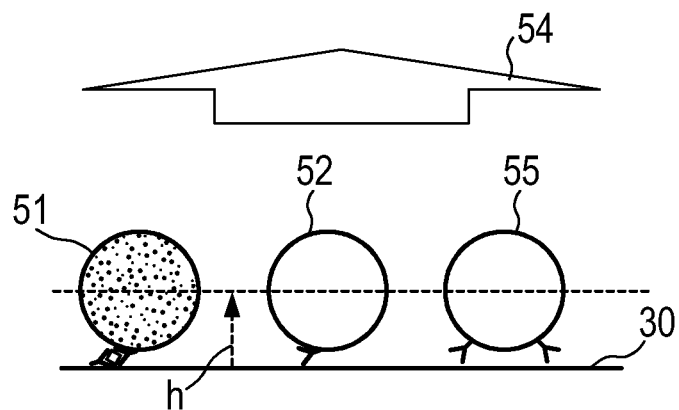
Figure 10:
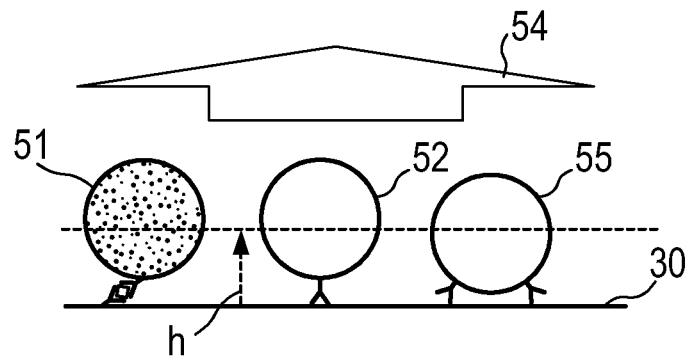
Figure 11:
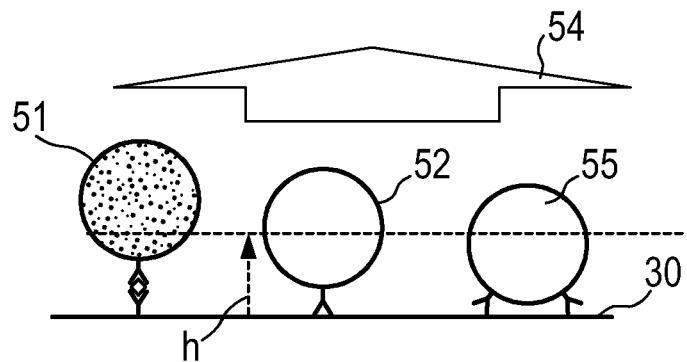

Then, as exemplarily illustrated in FIG. 8, the particles 51, 52, 55 are attracted towards the binding surface 30, i.e. in the direction indicated by the arrow 53. In this example the particle 51 is specifically bound, and the particles 52 and 55 are non-specifically bound, wherein the non-specific bindings of the particles 52 and 55 are different. In a next step, the particles are gently pulled away from the binding surface 30. This s schematically and exemplarily illustrated in FIG. 9. The measured sensing signal increases gradually as the average binding length increases. At a certain point in time the bindings of the particles 55 having the shortest binding length reach their maximum excursion from the binding surface 30, as shown in FIG. 9. In FIG. 9, the bindings of the particles 51, 52 are not completely stretched, while the binding of the particle 55 is completely stretched.

If the pulling force is further applied to the particles, then at a next point in time the particles 52 reach their maximum height and the sensing signal increases further. This situation is schematically and exemplarily illustrated in FIG. 10.

If the pulling force is further applied, finally all bindings are fully stretched. The sensing signal reaches its maximum value and the average binding length h is maximal. This situation is schematically and exemplarily illustrated in FIG. 11.

By assuming a constant velocity of the movement of the particles away from the binding surface 30, the sensing signal profile over time reflects the bond-length distribution. It should be noted that this kind of determining the bond-length distribution can also be performed by using DFM sensing signals.

Next to applying a force on the particles bound to the binding surface, which are preferentially magnetic particles, for moving the particles towards or away from the binding surface, forces can also applied to change the orientation of the particles. This is due to non-ideal magnetic properties, because the magnetic moment of an ideally superparamagnetic particle would always align with the field, thus making induction of an orientation change impossible. Non-ideal magnetic properties are, for example, a small permanent moment, magnetic grains with relatively long relaxation times or magnetic anisotropy. The force applying unit can therefore also be adapted to apply an orientation change to the magnetic particles bound to the binding surface. The force applying unit is preferentially adapted to apply an orientation change to the bound particles such that the height of the bound particles, i.e. the distance of the bound particles to the binding surface, is modulated. Thus, by applying an orientation change to the bound particles the distance between the particles bound to the binding surface and the binding surface can be modified. The particles can be magnetic particles having a diameter between 500 nm and 1000 nm and can be composed of a combination of polystyrene and a magnetic material.

A bound particle is generally able to sample a variety of heights due to Brownian motion, the degree of flexibility of the bond and the freedom of the bond to tilt or rotate. It is preferred to measure the bound particles both in a situation as close to the binding surface as possible and as far away from the binding surface as possible. This can be achieved by using external forces, for example, by applying magnetic forces for moving the particles towards or away from the binding surface as described above, in particular, by applying magnetic field gradients. However, for non-ideal magnetic particles, uncontrolled magnetic orientation may dominate the pulling force, thus leading to a different height than expected, in particular, leading to a different sensing signal, which depends on the distance between the bound particles and the binding surface, than expected. The force applying unit can therefore be adapted to control the magnetic orientation of the particles by controlling the magnetic field direction. By designing the force applying unit such that a desired field orientation can be achieved with respect to the particle orientation, specific behavior of particles can be induced.

Magnetic orientation can be exploited for two situations. In the first situation particles are bound via a target molecule, i.e. the substance, to the binding surface with a random magnetic orientation. This is, for example, the expected situation for a one step assay without using a magnetic field during binding. In order to obtain the desired magnetic orientation effects, a variety of field orientations have to be sampled. In the second situation the particles are bound with a controlled magnetic orientation. This can be performed by binding the particles via the target molecule, i.e. via the substance, to the binding surface under application of a magnetic field, in either a two-step assay, which is preferred, or a one step assay. In this case, a single magnetic field direction can be used in order to obtain the desired magnetic orientation effect.

Figure 12:
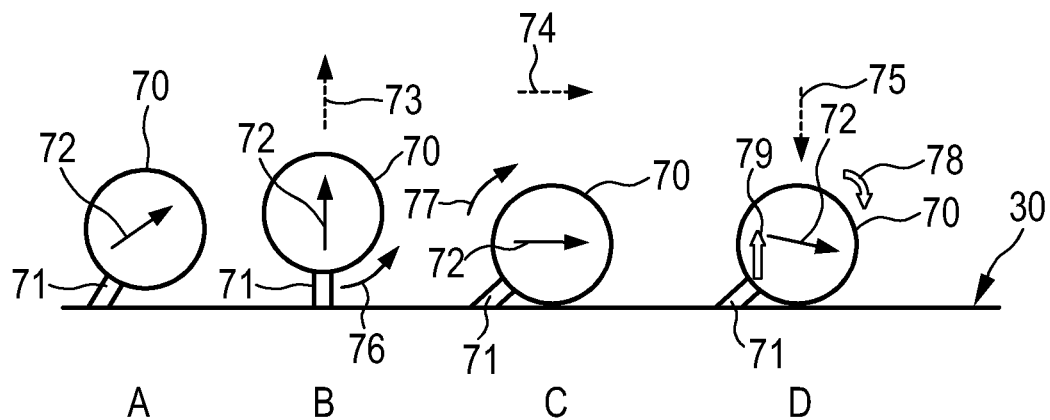
FIGS. 12 and 13 show schematically and exemplarily different orientations of a particle bound to the binding surface.

FIG. 12 illustrates schematically and exemplarily how the particle height, i.e. the distance of a particle to the binding surface, can be influenced using magnetic orientation. In the example indicated by the letter A, a magnetic field is not applied to the particle 70 and the movement of the particle is substantially only restricted by the binding 71 to the binding surface 30. In the example indicated in FIG. 12 by the letter B, a magnetic field 73 has been applied to the particle 70, thereby aligning the magnetic orientation 72 of the magnetic particle 70 with the magnetic field 73 and moving the particle 70 away from the binding surface 30. The magnetic field 73 turns the particle 70 in the direction indicated by the arrow 76 and stretches the bound 71. In the situation indicated in FIG. 12 by the letter C, the magnetic field 74 is oriented parallel to the binding surface 30 and the particle 70 is turned in the direction indicated by the arrow 77 towards the binding surface 30. The particle 70 is therefore moved towards the binding surface 30, thereby minimizing the particle height. In the situation indicated in FIG. 12 by the letter D, the magnetic field 75 is directed towards the binding surface 30, wherein a corresponding alignment of the magnetic orientation 72 with the magnetic field 75 is hindered by the binding surface 30. This hindering of the alignment results in a torque 78, which results in a leverage pulling force 79 on the bond 71.

The magnetic orientation effects can be combined with gradient forces for enhancing the effect of either of the two. For example, bounds that are still slightly flexible can then be stretched more.

Figure 13:
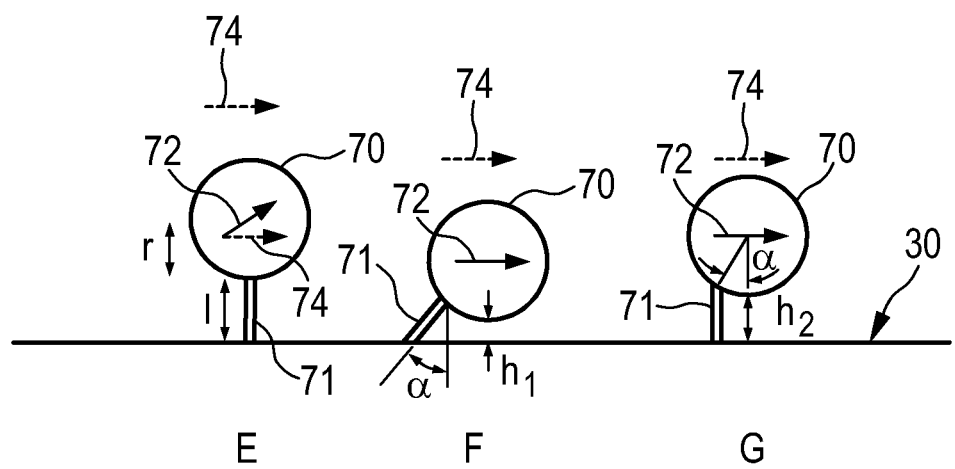

The change in the distance between the bound particles and the binding surface, i.e. the change in particle height, when the particle orients in the magnetic field, depends on the size of the particle and bond properties. FIG. 13 shows two extreme possibilities for the particle height to change when the particle magnetically orients in a magnetic field. The left part of FIG. 13 indicated by the letter E is used only for illustrating different variables like the length/of the bond 71 and the radius r of the particle 70. The magnetic field is indicated by 74 and the magnetic moment is indicated by 72.

In the orientation situation indicated in FIG. 13 by the letter F, the particle height can be defined by following equation:

$$h_1 = \cos\alpha(l+r) - r. \tag{28}$$

In the orientation situation indicated in FIG. 13 by the letter G, the particle height can be defined by following equation:

$$h_2 = l - r(1 - \cos\alpha). \tag{29}$$

The angle α is the rotation angle around the attachment point of the bond to the binding surface. In the situation indicated by the letter F the bond 71 and the particle 72 rotate together, whereas in the situation indicated by G the particle rotates with the same angle α around the attachment point between the bond and the particle.

Figure 14:
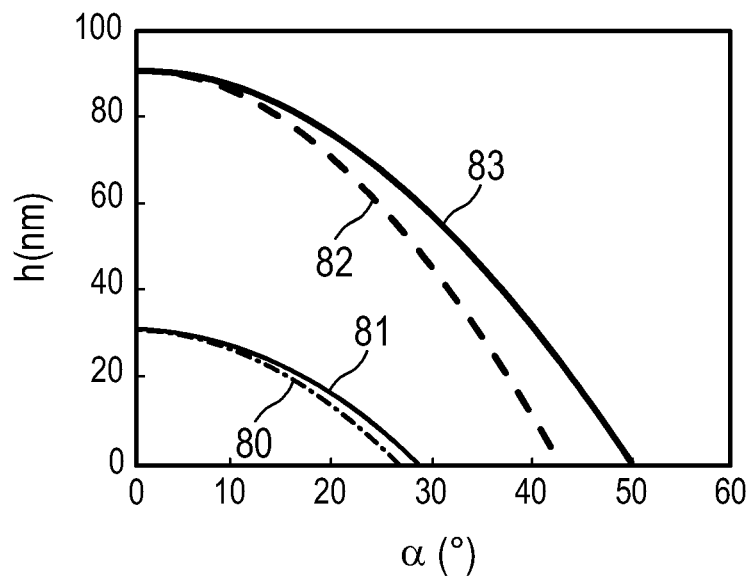
FIG. 14 shows schematically and exemplarily a dependence of the distance of bound particles to the binding surface on an orientation angle.

FIG. 14 shows schematically and exemplarily the dependence of the particle height h on the rotation angle In FIG. 14, line 80 indicates the height $h_1$ for a bond length of 30 nm, line 81 indicates the height $h_2$ for a bond length of 30 nm, line 82 indicates the height $h_1$ for a bond length of 90 nm, and line 83 indicates the height $h_2$ for a bond length of 90 nm. It can be seen that significant height changes occur for small rotation angles. The curves exemplarily shown in FIG. 14 are based on a radius of the particles of 250 nm.

Figure 15:
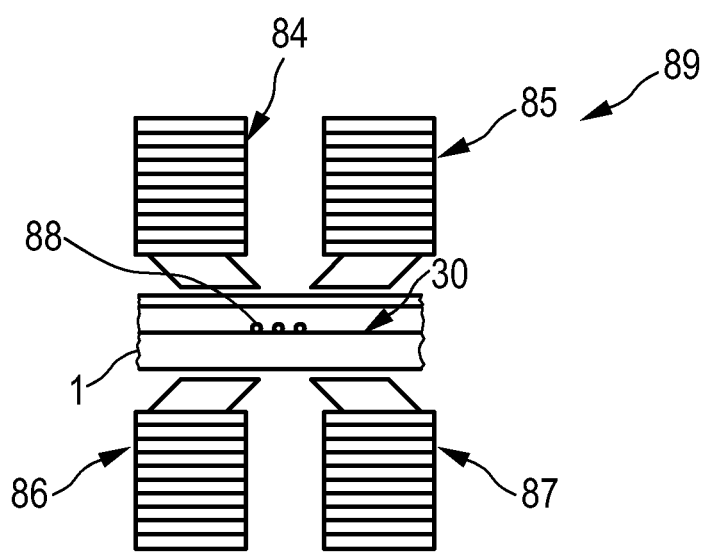
FIG. 15 shows schematically and exemplarily a force applying unit for applying magnetic forces to particles such that the orientation of the particles is modified.

FIG. 15 shows schematically and exemplarily a force applying unit 89 for applying magnetic forces to the magnetic particles 88 such that the orientation of the magnetic particles can be modified, thereby modifying the height of the magnetic particles 88 bound to the binding surface 30. The force applying unit 89 comprises four electromagnets 84, 85, 86, 87 for applying the magnetic field in the desired direction to the magnetic particles 88.

The force applying unit 89 is adapted to magnetically orient the magnetic particles 88, which are, in this embodiment, non-ideally superparamagnetic particles, for height modulation. A bound particle that rotates in a magnetic field, which can be regarded as an out-off-plane rotation, changes its height above the binding surface. The sensing unit is preferentially adapted to generate a first sensing signal depending on a first distance between the particles bound to the binding surface and the binding surface and to generate a second sensing signal depending on a second distance between the particles bound to the binding surface and the binding surface, wherein the first distance and the second distance are different, in particular, because of different magnetic orientations of the magnetic particles induced by the force applying unit. The specific binding determination unit is preferentially adapted to determine the specifically bound particles depending on the first sensing signal and the second sensing signal.

It should be noted that the force applying unit 89 shown in FIG. 15 is part of an analyzing device for cooperating with the binding device 1, i.e. the cartridge 1, for determining a substance within a fluid. Thus, the force applying unit 89 shown in FIG. 15 can be used instead of or in addition to the magnetic unit 23, 24 in the substance determining apparatus described above with reference to FIG. 4.

Although in the above described embodiments force has been applied to the particles bound to the binding surface by magnetic forces, in other embodiments, in addition or alternatively, the force applying unit can be adapted to apply another kind of force to the particles bound to the binding surface. For example, the force applying unit can be adapted to apply a fluidic force or an electrostatic force to the particles bound to the binding surface.

In an embodiment, the force applying unit is adapted to use electrostatic forces to push particles bound to the binding surface away from the binding surface. This can be performed by exchanging the fluidic buffer in a fluidic wash step, while the particles remain bound to the binding surface.

Both, the particles and the binding surface, have an electrostatic surface charge in the fluid due to absorption of ions from the fluid or dissociation of surface groups on the surfaces. Typically, in biosensor environments, the surface charge is negative for both the particles and the binding surface, leading to a natural repulsion between particles and binding surface. Ions in the fluid can screen the charge of both surfaces, thereby decreasing the repulsion.

The layer over which screening takes place is called the double layer. The inverse double layer thickness x, correlated to the Debye-Hueckel length $\lambda_D$ ($\lambda_D = \kappa^{-1}$), is given by:

$$\kappa = \sqrt{\frac{2000\, e^2 N_A I_C}{\varepsilon_0 \varepsilon_r k_B T}}, \tag{30}$$

where e is the elementary charge, $N_A$ Avogadro's number, $I_C$ the ionic strength of the fluid, $\varepsilon_0$ the dielectric permittivity of free space, $\varepsilon_r$ the relative permittivity of the fluid and $k_B T$ the thermal energy.

The electrostatic interaction energy between a particle and a surface depends on the inverse double layer thickness and is given by:

$$E_{es} = ZR \cdot \exp(-\kappa h), \tag{31}$$

with R the particle radius, h the distance between the particle (bottom) and the surface and Z given by:

$$Z = 64\pi\varepsilon_0\varepsilon_r \left(\frac{k_B T}{e}\right)^2 \tanh\left(\frac{ze\Psi_{particle}}{4k_B T}\right) \tanh\left(\frac{ze\Psi_{surface}}{4k_B T}\right). \tag{32}$$

Here z is the electrolyte valence, and $\Psi_{particle}$ and $\Psi_{surface}$ the surface potentials of respectively the particle and the surface. The electrostatic force between a particle bound to the binding surface and the binding surface depends therefore on the ionic strength of the buffer and can be increased by decreasing the ion concentration in the fluid. Thus, by modifying the ion concentration in the fluid, the distance between the particles bound to the binding surface and the binding surface can be modified. The force applying unit can therefore be adapted such that the ion concentration in the fluid can be modified. The ion concentration can, for example, be changed by inserting a new fluid in the binding device such that the new fluid is present on the binding surface. For example, the analyzing device can be adapted to fill a new fluid into the binding device, which is preferentially a cartridge, along the same way which has been used for transferring the original fluid like the blood to the binding surface.

Generally, also the Van der Waals interaction is present between the particles bound to the binding surface and the binding surface. The Van der Waals interaction can be expressed by following equation:

$$E_{vdw} = -\frac{1}{6}A_{132}\left[\frac{R}{h} + \frac{R}{h+2R} + \ln\left(\frac{h}{h+2R}\right)\right] \quad (33)$$

with $A_{132}$ the Hamaker constant of a particle of material 1 on a surface of material 2 in a fluid of material 3. The value of the Hamaker constant is usually around a few $k_BT$, and can be positive (attractive) or slightly negative (repulsive, mainly due to the presence of proteins on the surfaces). The force between the particles bound to the binding surface and the binding surface is the negative gradient of the respective interaction term, i.e. e.g. the negative gradient of $E_{es}$ and $E_{vdw}$.

By varying the Hamaker constant, for example, by exchanging the fluid, the Van der Waals interaction between the bound particles and the binding surface and, thus, the distance between the bound particles and the binding surface can be modified.

Some typical values for the Debye length $\lambda_D$ are plotted in the table below. Also calculated is the distance over which the electrostatic energy increases $3k_BT$ from the energy minimum (probability that the particle reaches this distance is less than 5%). Typical values are taken of −35 mV for both $\psi_{particle}$ and $\psi_{surface}$, 80 for the relative permittivity of water of and z=1 for the electrolyte valence. The final two columns shows the same calculation as for the third column, but then also taking into account the Van der Waals energy, which may be attractive or repulsive.

| $I_c$ (M) | $\lambda_D$ (nm) | $E_{es}/3\ k_BT$ (nm) | $E_{es} + E_{vdw}/3\ k_BT$ (nm) $A_{132} = 2\ k_BT$ | $E_{es} + E_{vdw}/3\ k_BT$ (nm) $A_{132} = -1\ k_BT$ |
|---|---|---|---|---|
| 0.1 | 1 | 5 | 3 | 12 |
| 0.1/4 | 2 | 10 | 9 | 13 |
| 0.1/16 | 4 | 21 | 19 | 23 |
| 0.1/64 | 8 | 41 | 36 | 43 |
| 0.1/256 | 16 | 82 | 80 | 84 |

These calculations thus show that when diluting the buffer large electrostatic repulsion can be achieved. For example, a particle bound with a bond length of 100 nm will have a minimum height of around 80 nm at a ionic concentration of 0.1/256=0.4 mM, so will be considerably stretched.

In this model, electrostatic repulsion forces that can be achieved are for example:

| 0.1/16 = 6 mM | >10 pN for distances <16 nm |
| | >50 pN for distances <10 nm |
| 0.1/256 = 0.4 mM | >10 pN for distances <43 nm |
| | >50 pN for distances <18 nm |
| 0.1/1024 = 0.1 mM | >10 pN for distances <65 nm |
| | >50 pN for distances <15 nm |

In the previous table, the first column give various dilutions of a 0.1 M buffer, for example, 0.1/16 is 16-times diluted resulting in a molarity of 6 millimolar. The second column shows exemplarily which magnetic forces can be created at which distances. It can be seen that in this example forces of 50 pN have been reached. Since the forces by which the particles are bound to the binding surface are typically also in this range, the electrostatic repulsion forces are large enough for modifying the height of the particles. It should be noted that in other embodiments larger or smaller electrostatic repulsion forces can be generated for modifying the height of the particles.

These calculations show also that the effect of particle-particle interaction is very small. Because of the exponential decay of electrostatic interaction, and because the typical Debye lengths are small (1-16 nm), electrostatic particle-particle interaction becomes negligible for distances larger than 100 nm. For magnetic interaction the energy decays much less strongly, with a third power dependence, thus leading to high magnetic dipole forces even over micrometers distance. Particle height modulation by buffer exchange thus gives a strong single particle approach.

The force applying unit can therefore be adapted to use electrostatic forces to pull bound particles away from the binding surface. This can be done by exchanging the fluidic buffer, while the particles remain bound to the binding surface, in a fluid wash step. Thus, a first sensing signal can be generated while a first fluidic buffer is present at the binding surface and a second sensing signal can be generated while a second fluidic buffer is present on the binding surface, wherein the first fluidic buffer and the second fluidic buffer are chosen such that the distance of the bound particles to the binding surface is different, while the first fluidic buffer is used, in comparison to the distance between the bound particles and the binding surface, while the second fluidic buffer is used. The specific binding determination unit can be adapted to determine specifically bound particles, in particular, the part of the generated first sensing signal or the generated second sensing signal, which is caused by the specifically bound particles, depending on the generated first sensing signal and on the generated second sensing signal.

Referring again to FIG. 4, the substance determination apparatus 19 is comprised of the binding device 1 and the analyzing device 18. The binding device 1 is, in this embodiment, a cartridge including the particles, and the binding surface and being adapted to receive the fluid 3. The analyzing device 18 can be regarded as a reader and includes the sensing unit 33 and the specific binding determination unit 34. The binding device 1 is a disposable device and the analyzing device 18 is a re-useable device.

The analyzing device 18 further comprises an output unit 60 for outputting a value indicating the amount or concentration of the substance within the fluid. The output unit 60 is preferentially a display. The analyzing device 18 further comprises a control unit 61 for controlling the sensing unit 33, the specific binding determination unit 34 and the output unit 60.

The specific binding determination unit 34 is preferentially adapted to determine specifically bound particles by determining the contribution of the specifically bound particles to the sensing signal. The specific binding determination unit 34 is preferentially further adapted to determine a concentration of the substance within the fluid based on the determined contribution of the specifically bound particles to the generated sensing signal. Preferentially, the specific binding determination unit 34 comprises assignments between determined contributions of specifically bound particles to the generated sensing signals and concentrations of the substance in the fluid. These assignments are preferentially generated by calibration and can be stored in the specific binding determination unit 34 in tabular form or as a function.

As already mentioned above, the binding device 1 is preferentially a cartridge for receiving a fluid like blood, saliva or urine, for filtering the fluid and for transferring the filtered fluid to the sensing site of the cartridge. The cartridge is disposable and is adapted for single use only. The analyzing device 18 is adapted to be used several times with different cartridges. Thus, a fluid 3 like blood, saliva or urine is put on the filter element 2 of the binding device 1, the fluid 3 is filtered and the filtered fluid is transferred to the sensing location 7. The binding device 1, i.e. in this embodiment the cartridge, is arranged in the analyzing device 18 and a substance within the fluid 3 at the sensing location is analyzed by the analyzing device 18. After the binding device 1 has been used, it is preferentially discarded, whereas the analyzing device 18 is used for a next analyzing procedure.

Figure 16:
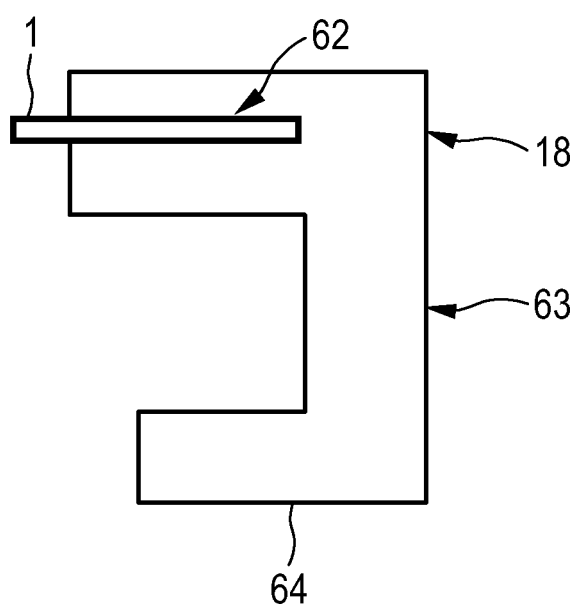
FIG. 16 shows schematically and exemplarily a binding device introduced into an analyzing device.

The several units of the analyzing device 18 are preferentially arranged within a casing 64, which is schematically and exemplarily shown in FIG. 16 and which can comprise a grip part 63 for allowing a user to hold the analyzing device 18 in the hand while analyzing the substance in the fluid. The casing 64 comprises a receiving section 82 for receiving the binding device 1. In other embodiments, the casing 64 can have another shape.

Figure 17:
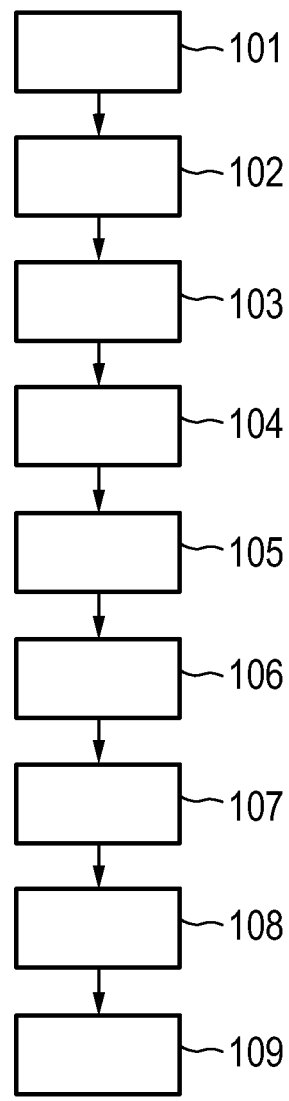
FIG. 17 shows a flowchart exemplarily illustrating a substance determining method for determining a substance in a fluid.

In the following a substance determining method for determining a substance within a fluid will exemplarily be described with reference to a flowchart shown in FIG. 17.

In step 101, a fluid sample, in particular, a blood sample, is arranged on the filter element 2.

In step 102, the fluid is filtered by the filter element 2, and in step 103 the filtered fluid is transferred to the sensing location by capillary forces generated by the connecting channel and the guiding channels of the capillary structure.

Before, while or after performing steps 101 to 103 the binding device 1 has been introduced into the analyzing device 18. At the sensing location 7 magnetic particles coated with a specific antibody that attaches to a target molecule present in the fluid are located. They mix with the filtered fluid, and the magnetic particles with the specific antibody attach to the target molecules within the fluid in step 104.

In step 105, the magnetic unit is controlled such that the magnetic particles at the sensing location are forced onto the binding surface. The magnetic particles with the attached target molecules bind to the binding surface and in step 106 the magnetic unit is controlled such that magnetic forces pull the magnetic particles, which have not bound to the binding surface, away from the one or several sensing sites so that only the bound magnetic particles stay attached to the binding surface. The bound particles are specifically bound particles and non-specifically bound particles.

In step 107, the particles on the binding surface are sensed, wherein a sensing signal is generated being indicative of a distance between the particles bound on the binding surface and the binding surface. This sensing step can generate the sensing signals as described in the above mentioned embodiments. For example, a first and second FTIR sensing signal can be measured with different evanescent fields and/or first and second DFM sensing signals can be generated with different evanescent fields. Moreover, different sensing signals can be generated while different forces are applied to the bound particles, for example, while the particles are attracted towards the binding surface and while the particles are pulled away from the binding surface.

In step 108, specifically bound particles being particles bound to the binding surface, which have been attached to the substance, are determined depending on the generated sensing signals. In particular, the part of the sensing signals caused by the specifically bound particles is determined and this part is related to an amount of specifically bound particles and/or a concentration of the substance within the fluid by using assignments between part of the sensing signals caused by the specifically bound particles and the amount of specifically bound particles and/or the concentration of the substance within the fluid, respectively In step 109, the determined amount of specifically bound particles and/or the concentration of the substance within the fluid is displayed to a user.

Steps 101 to 106 can be regarded as the steps of a binding method, and steps 107 to 109 can be regarded as the steps of an analyzing method.

The substance determining apparatus is preferentially a magnetic biosensor that can be used to determine the height of bound particles above the binding surface, in particular, in order to correct for non-specific binding. The substance determining apparatus is preferentially based on nanoparticles that can be actuated with electro-magnetic fields. The nanoparticles are preferentially magnetic beads which are functionalized with antibodies that can bind a specific analyte molecule. The beads are attracted to the binding surface, where the number of bound beads is directly or inversely related to the amount of analyte molecules present in the fluid sample. The beads are then preferentially detected by using a technique that is more sensitive to beads that are close to the binding surface than to beads that are more far away from the binding surface. The substance determining apparatus uses preferentially the above described FTIR technique and/or DFM technique. Using these techniques, the sensitivity to the nano particles decreases exponentially with an increasing distance from the surface. Generally, if the distance between the particles and the binding surface is larger, the corresponding sensing signal will be smaller. However, the sensing signal can also be defined such that a particle being closed to the binding surface generates a smaller signal then a particle being more far away from the binding surface.

To increase the sensitivity of the assays performed on a biosensor, many efforts are made to increase the signal obtained per bead. However, when measuring very low analyte concentrations, the sensitivity is ultimately determined by the signal that is obtained for a low concentration and the signal that is obtained for a blank measurement, containing no analyte. It has been observed that the signal for the blank is not only determined by the instrument noise, but that additional signal is generated by beads binding to the surface, independent of the presence of analyte (non-specific binding). If this specific binding occurs (which it typically does), increasing the signal per bead does not increase the sensitivity, as the signal for the specific binding is also increased.

Additives in the sample fluid or "blocking" the surface with an inert protein that prevents bead/protein binding to accessible parts of the sensor surface material can be used for suppressing the non-specific binding. However, this is an arduous and expensive process of trial-and-error.

The substance determining apparatus in accordance with the invention allows to distinguish between specific and non-specific binding without using and arduous expensive processes.

The DFM sensing signals preferentially allow measuring the bond length and/or the bond strength on an individual particle basis, thereby allowing a discrimination between specifically and non-specifically bound particles.

Magnetic beads with a diameter of 500 nm are visible under a microscope with sufficient magnification and resolution. Therefore, the surface density of beads can be determined by counting the number of individual beads within the field of view. For example, when the field of view has an area of 1 mm$^2$, the lowest measurable surface density is 1 bead/1 mm$^2$ or 1 bead/10$^6$ um$^2$. With regard to a minimal detectable surface density of 1 bead/200 um$^2$, such a counting method results in an increase in sensitivity of a factor of 5000. This brings the minimum detectable target concentration within the region of interest (for example 1 fM). Single bead detection offers an enhancement of the sensitivity by at least 2 to 3 orders of magnitude. Since beads are detected 'digitally', the method is insensitive to drift.

In a normal microscope where front side or backside illumination sources are used, no or little accurate information is obtained about the height of the bead above the surface. In the FTIR setup height information is present in the signal because the beads are located in a more or less exponential decaying evanescent field. The decay length of the evanescent field is in the order of 50-150 nm. Changes in the height position in the order of a few nanometers are therefore detectable by this system. Height and/or height changes can provide valuable information about the binding state of the bead.

FIG. 4 proposes a (handheld or table top) configuration which integrates FTIR measurement, single bead optical detection with FTIR illumination and magnetic actuation all positioned at one side of the cartridge. In this way an increase in sensitivity is obtained while simultaneously information about the binding state of individual beads can be collected allowing better discrimination between the signal from specifically and non-specifically bound beads. The other side (top) of the cartridge remains fully accessible, allowing the positioning of a (second) washing magnet, a heater for temperature control or other devices.

The binding device is preferentially an optical cartridge being a carrier of a bioassay comprising particles being optical labels, preferably microscopic superparamagnetic labels providing optical contrast by means of scattering and/or fluorescence.

Although in the above described embodiments total internal reflection has been used for inducing the evanescent field, in other embodiments other techniques can be used for inducing the evanescent field, for example, grating coupling or waveguide coupling can be used.

Although in the above mentioned embodiment described with reference to FIG. 4, a microscope objective 32 has been used, in other embodiments another objective lens for collecting and imaging of photons can be used. This objective lens is positioned at the bottom side of the binding device, underneath the horseshoe actuation magnet 23. The photons from the optical labels are transmitted through an air gap in between the two horseshoe magnets 23, before they are captured by the objective lens. The objective lens has a numerical aperture allowing imaging the individual optical labels onto the second light detector 27 being, for example, a CCD camera.

The substance determining apparatus is preferentially adapted to allow determining for each individual particle whether the particle is specifically or non-specifically bound on the binding surface, or to determine the fraction of non-specifically bound particles from an assemble of particles.

Although in the above described embodiments the particles are magnetic particles, in other embodiments other particles can be used like fluorescent particles.

Although a certain linker molecule has been described above with reference to FIG. 6, the linker molecule can also be an integral part of an antibody or of another binding molecule if, for example, a polypeptide sequence is added to a recombinant antibody.

Although in the above described embodiments the substance determining apparatus comprises means for generating FTIR sensing signals and DFM sensing signals, in other embodiments the substance determining apparatus can be adapted such that it comprises only one of these means, i.e. means for generating FTIR sensing signals or means for generating DFM sensing signals.

Although in a described embodiment the analyzing device is a handheld device, in other embodiments the analyzing device can also be a standalone system which is to be arranged on, for example, a table.

Although in the above described embodiments, specifically bound particles have been determined, in particular, although it has been described that the measured sensing signals are used for discriminating specifically and non-specifically bound particles, the substance determining apparatus, in particular, the binding discrimination unit, can also be used to discriminate between different kinds of binding. That means, the binding discrimination unit can be used to determine the amount or concentration of particles that are bound to the binding surface via a certain binding.

Although in the above described embodiments it has been described that a first sensing signal is generated while the particles are moved away from the binding surface and a second sensing signal is generated while the particles are moved towards the binding surface, in further embodiments, the first and second sensing signals can be generated in other conditions, for example, a first sensing signal can be generated while the particles are moved in a first lateral direction and the second sensing signal can be generated while the particles are not moved in the first lateral direction or moved in a second lateral direction being different to the first lateral direction.

In the above described embodiment, the fluid was preferentially blood. In other embodiments, the fluid can be any other fluid, in particular, another body fluid, like saliva or urine. The preferred application for the binding device and for the analyzing device is in the field of point-of-care diagnostics, in particular, based on a finger prick blood sample, like a cardiac marker detection application. But, as mentioned above, the binding device can also be adapted for being used with other fluids like saliva for Drugs Of Abuse.

In the above described embodiments, the analyzing device apparatus uses evanescent field techniques for determining the amount of magnetic beads on the surface. In other embodiments, other techniques can be used for determining these beads. For example, magnetic methods, sonic detection, electrical detection and combinations therefore can be used. Furthermore, the analyzing device can comprise any sensor based on the detection of the magnetic properties of the beads on or near to a sensor surface. The analyzing device can be adapted for detecting molecular targets, which often determine the concentration and/or presence of larger moieties, for example, cells, viruses, fractions of cells or fractions of viruses, tissue extract et cetera. The magnetic beads can be detected directly by the sensing method. As well, the particles can be further processed prior to detection. An example of further processing is that materials are added or that the chemical, biochemical or physical properties of the magnetic labels are modified to facilitate detection. The analyzing device can be adapted for working together with several biochemical assay types, for example, binding/unbinding assay, sandwich assay, competition assay, displacement assay, enzymatic assay et cetera. The binding device and the analyzing device can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The binding device and the analyzing device can be used as rapid, robust and easy to use point-of-care biosensors for small sample volumes. The sensing cavity is preferentially a part of a disposable cartridge, which is to be used with the analyzing device, which contains one or more magnetic field generating means, i.e. the magnetic unit, and one or more detection means. The binding device and the analyzing device can preferentially be adapted for a use in automated high-throughput testing.

The particles are preferentially magnetic beads being preferentially nanoparticles having at least one dimension ranging between 3 nm and 5000 nm, preferably between 10 nm and 3000 nm, more preferred between 50 nm and 1000 nm.

Although in the above described embodiments a certain binding device and a certain analyzing device have been described, in other embodiments, the binding device and the analyzing device can have another structure. For example, the binding device can just comprise a binding surface. Or another kind of filter can be used or another channel structure can be used for transferring filtered fluid from a filter location to a sensing location.

Although in the above described embodiments the substance determining apparatus is comprised of a binding device and an analyzing device, in another embodiment the substance determining apparatus can be an integrated apparatus comprising at least the particles, the binding surface, the sensing unit and the specific binding determination unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The control of the substance determining apparatus, in particular, of the analyzing device, in accordance with the substance determining method, in particular, in accordance with the analyzing method, can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a substance determining apparatus for determining a substance within a fluid. Particles, which have attached the substance, are bound to a binding surface. A sensing unit is adapted to generate a sensing signal being indicative of at least one of i) a distance between the particles bound on the binding surface and the binding surface and ii) an in-plane position of the particles bound on the binding surface. A binding discrimination unit is adapted to discriminate between different kinds of binding of the particles bound on the binding surface depending on the generated sensing signal. The binding discrimination unit is preferentially a unit for determining the part of the sensing signal being caused by specifically bound particles and to determine the substance based on this determined part of the sensing signal.

The invention claimed is:

1. A substance determining apparatus for determining a substance within a fluid, the substance determining apparatus comprising:
   a binding device including a binding surface and particles configured to be attached to the substance within the fluid;
   the binding surface being configured to bind the particles attached to the substance; and
   an analyzing device including:
   a sensor configured to:
      sense the particles bound on the binding surface,
      generate a sensing signal being indicative of at least one of i) a distance between the particles bound on the binding surface and the binding surface and ii) an in-plane position of the particles bound on the binding surface, wherein the sensor comprises a light source configured to generate radiation and direct the radiation to the binding surface, and wherein the radiation includes a first wavelength and a second wavelength;
   a binding discrimination unit configured to discriminate between different kinds of binding of the particles bound on the binding surface depending on the sensing signal including light being scattered from the particles bound on the binding surface;
   a display configured to display an indication of presence of the substance; and
   a memory configured to store instructions that configure the analyzing device to determine the substance within a fluid by controlling at least one of the sensor, the binding discrimination unit and the display,
   wherein the sensor is configured to:
      modify at least one of i) the distance between the particles bound to the binding surface and the binding surface, ii) the in-plane position of the particles bound on the binding surface and iii) a distance sensitivity of the sensing unit, wherein the distance sensitivity is indicative of the dependence of the sensing signal on the distance between the particles bound to the binding surface and the binding surface,
      generate a first sensing signal depending on at least one of i) a first distance between the particles bound to the binding surface and the binding surface, ii) a first in-plane position of the particles bound on the binding surface and iii) a first distance sensitivity, and
      generate a second sensing signal depending on at least one of i) a second distance between the particles bound to the binding surface and the binding surface, ii) a second in-plane position of the particles bound to the binding surface and iii) a second distance sensitivity,
   wherein the binding discrimination unit is configured to:
   discriminate between the different kinds of the binding depending on the first sensing signal and the second sensing signal, discriminate between the different kinds of the binding depending on a ratio of the first sensing signal and the second sensing signal, determine a part of the sensing signal caused by specifically bound particles as a ratio having a numerator and a denominator and determine the substance based on the ratio, wherein the numerator is a difference between i) the first sensing signal and ii) a product of a non-specific ratio and the second sensing signal, and wherein the denominator is a difference between i) the first and ii) a ratio of the non-specific ratio and a specific ratio, determine the specific ratio by generating the first sensing signal and the second signal while the substance is present in the fluid, and determine the non-specific ratio by generating the first sensing signal and the second sensing signal while the substance is not present in the fluid.

2. The substance determining apparatus of claim 1, wherein the radiation from the light source having the first wavelength and the second wavelength generates an evanescent field, and wherein the sensor further comprises a light detector configured to detect light from the binding surface and being indicative of an influence of the particles on the evanescent field, wherein the sensor is configured to:

generate the sensing signal based on the detected light, modify the spatial relationship between the evanescent field and the particles bound to the binding surface by modifying at least one of i) the distance between the particles bound on the binding surface and the binding surface, ii) the in-plane position of the particles bound on the binding surface, and iii) the distance sensitivity, generate the first sensing signal depending on a first spatial relationship between the evanescent field and the particles bound to the binding surface, and generate the second sensing signal depending on a second spatial relationship between the evanescent field and the particles bound to the binding surface, and wherein the light detector is configured to detect the light being scattered from the particles bound on the binding surface.

3. The substance determining apparatus of claim 1, wherein the indication of presence of the substance includes one of and amount and a concentration of the substance within the fluid.

4. The substance determining apparatus of claim 1, further comprising a magnetic unit configured to generate a rotating magnetic field for applying a force to the particles.

5. The substance determining apparatus of claim 4, wherein the force is such that the particles are attracted towards the binding surface or pulled away from the binding surface.

6. The substance determining apparatus of claim 1, wherein the sensor comprises a force applying unit configured to apply a force to the particles bound to the binding surface, wherein the sensor is configured to modify at least one of i) the distance between the particles bound to the binding surface and the binding surface and ii) the in-plane position of the particles bound on the binding surface by modifying the force applied to the particles bound on the binding surface.

7. The substance determining apparatus of claim 6, wherein the force applying unit is configured to move the particles towards the binding surface and move the particles in a direction away from the binding surface, wherein the sensor is configured to generate a first detected signal if the particles bound to the binding surface have been moved towards the binding surface and generate a second detected signal if the particles bound to the binding surface have been moved in a direction away from the binding surface, and generate several detected signals over time while the particles bound to the binding surface are moved in a direction away from the binding surface, and wherein the binding discrimination unit is configured to discriminate between different kinds of binding depending on the several detected signals generated over time.

8. The substance determining apparatus of claim 6, wherein the force applying unit is configured to use electrostatic forces to push particles bound to the binding surface away from the binding surface by exchanging the fluidic buffer in a fluidic wash step.

* * * * *